US012727934B2

(12) United States Patent
Scheller et al.

(10) Patent No.: US 12,727,934 B2
(45) Date of Patent: Sep. 8, 2026

(54) BIPOLAR FORCEPS

(71) Applicant: Kogent Surgical, LLC, Chesterfield, MO (US)

(72) Inventors: Gregg D. Scheller, Wildwood, MO (US); Clayton Chatman, Chesterfield, MO (US)

(73) Assignee: KOGENT SURGICAL, LLC, Chesterfield, MO (US)

( * ) Notice: Subject to any disclaimer, the term of this patent is extended or adjusted under 35 U.S.C. 154(b) by 289 days.

(21) Appl. No.: 18/483,354

(22) Filed: Oct. 9, 2023

(65) Prior Publication Data

US 2024/0032988 A1 Feb. 1, 2024

Related U.S. Application Data

(63) Continuation-in-part of application No. 16/284,324, filed on Feb. 25, 2019, now abandoned, which is a (Continued)

(51) Int. Cl.

| | |
|---|---|
| ***A61B 18/14*** | (2006.01) |
| ***A61B 17/29*** | (2006.01) |
| *A61B 18/00* | (2006.01) |

(52) U.S. Cl.

CPC ...... *A61B 18/1445* (2013.01); *A61B 17/2909* (2013.01); *A61B 18/1442* (2013.01);

(Continued)

(58) Field of Classification Search

CPC ............ A61B 17/2909; A61B 18/1442; A61B 18/1445; A61B 2018/00083;

(Continued)

(56) References Cited

U.S. PATENT DOCUMENTS

| | | | |
|---|---|---|---|
| 3,100,489 | A | 8/1963 | Bagley |
| 5,674,220 | A | 10/1997 | Fox et al. |

(Continued)

FOREIGN PATENT DOCUMENTS

| | | | |
|---|---|---|---|
| EP | 1709923 | A2 | 10/2006 |

OTHER PUBLICATIONS

Dujovny et al., Bipolar Jeweler's Forceps With Automatic Irrigation, for Coagulation in Microsurgery, Plastic and Reconstructive Surgery, Nov. 1975 (3 pages).

(Continued)

*Primary Examiner* — Khadijeh A Vahdat

(74) *Attorney, Agent, or Firm* — NIXON PEABODY LLP

(57) ABSTRACT

A surgical instrument for electrosurgery having a first forceps arm, a first forceps jaw of the first forceps arm, a first conductor tip of the first forceps arm, a second forceps arm disposed opposite the first forceps arm, a second forceps jaw of the second forceps arm, the second forceps jaw disposed opposite the first forceps jaw, a second conductor tip of the second forceps arm, and the second conductor tip disposed opposite the first conductor tip. The first forceps arm and the second forceps arm are configured to transfer thermal energy away from the first conductor tip and second conductor tip at a rate sufficient to maintain the thermal energy of the first conductor tip and second conductor tip below a designated thermal threshold. The first and second forceps arms being composed of a zirconium copper alloy.

24 Claims, 23 Drawing Sheets

Related U.S. Application Data continuation-in-part of application No. 15/697,930, filed on Sep. 7, 2017, now abandoned, which is a continuation of application No. 15/242,696, filed on Aug. 22, 2016, now Pat. No. 9,801,680, which is a continuation of application No. 14/694,659, filed on Apr. 23, 2015, now Pat. No. 9,452,012, which is a continuation of application No. 13/742,120, filed on Jan. 15, 2013, now Pat. No. 9,044,242.

(52) U.S. Cl.
CPC ............... *A61B 2018/00083* (2013.01); *A61B 2018/00107* (2013.01); *A61B 2018/00589* (2013.01); *A61B 2018/00595* (2013.01); *A61B 2018/0063* (2013.01)

(58) Field of Classification Search
CPC A61B 2018/00095; A61B 2018/00107; A61B 2018/00148; A61B 2018/00178; A61B 2018/00589; A61B 2018/00595; A61B 2018/0063; A61B 2018/1462
See application file for complete search history.

(56) References Cited

U.S. PATENT DOCUMENTS

| | | | | |
|---|---|---|---|---|
| 6,050,996 | A | 4/2000 | Schmaltz et al. | |
| 6,231,574 | B1 | 5/2001 | Posthuma | |
| 6,293,946 | B1 | 9/2001 | Thorne | |
| 6,482,205 | B1 | 11/2002 | Bonnet | |
| 6,679,881 | B1 | 1/2004 | Bybee | |
| 6,749,610 | B2 | 6/2004 | Kirwan, Jr. et al. | |
| 6,767,348 | B2 | 7/2004 | Nakada et al. | |
| 6,860,882 | B2 | 3/2005 | Battles et al. | |
| 7,122,035 | B2 | 10/2006 | Canady | |
| 7,150,097 | B2 | 12/2006 | Sremcich et al. | |
| D559,984 | S | 1/2008 | Scheller | |
| 7,736,361 | B2 | 6/2010 | Palanker et al. | |
| 7,867,230 | B2 | 1/2011 | Asahara et al. | |
| 7,963,965 | B2 | 6/2011 | Buysse et al. | |
| 8,048,107 | B2 | 11/2011 | Chen | |
| 8,108,994 | B2 | 2/2012 | Ariola, Jr. et al. | |
| 8,192,433 | B2 | 6/2012 | Johnson et al. | |
| 8,211,105 | B2 | 7/2012 | Buysse et al. | |
| 2005/0107784 | A1 | 5/2005 | Moses et al. | |
| 2006/0235466 | A1* | 10/2006 | McGarity | A61B 17/02 606/205 |
| 2007/0265619 | A1* | 11/2007 | Ariola | A61B 18/1442 606/51 |
| 2008/0200914 | A1* | 8/2008 | Hanlon | A61B 18/1442 606/48 |
| 2011/0009856 | A1* | 1/2011 | Jorgensen | A61B 18/1492 606/33 |
| 2012/0004653 | A1 | 1/2012 | Butsch | |
| 2013/0066317 | A1 | 3/2013 | Evans et al. | |
| 2017/0291246 | A1* | 10/2017 | Sigler | B23K 11/20 |

OTHER PUBLICATIONS

Dujovny et al., Bipolar Coagulation in Neurosurgery, Surg. Neural. 1998; (5 pages).
Malis, Electrosurgery and Bipolar Technology, Operative Neurosurgery, No. 1, vol. 58, Feb. 2006 (12 pages).
Olsen Medical; "Single Use Bipolar Forceps" 2008 (2 pages).
Vellimana et al., Current Technological Advances of Bipolar Coagulation, Operative Neurosurgery, No. 1, vol. 64, Mar. 2009 (9 pages).
Elliott-Lewis et al., Evaluation of New Bipolar Coagulation Forceps in a Thermal Damage Assessment, Operative Neurosurgery, No. 6, vol. 65, Dec. 2009 (6 pages).
Elliott-Lewis et al., Thermal Damage Assessment of Novel Bipolar Forceps in a Sheep Model of Spinal Surgery, Neurosurgery 67, 2010 (7 pages).
Stingray Surgical Products, Inc. Reusable Bipolar Forceps; Brochure, 2010 (24 pages).
Soring Product Catalog; Zubehor Accessories; Sep. 2011 (52 pages).
Sutter, "Supergliss Non-Stck Bipolar Forceps" 2012 (12 pages).
Aesculap; Instruments and Devices for Bipolar Surgery; Aesculap Neurosurgery; 2012 (34 pages).

* cited by examiner

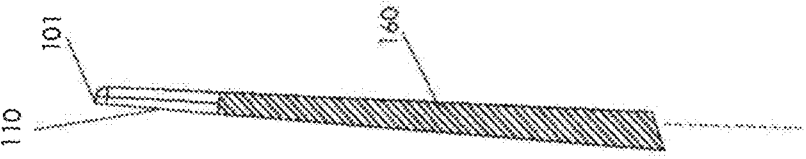
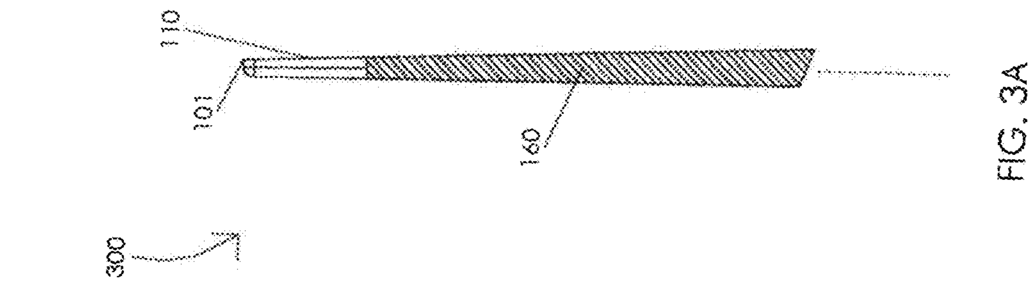
FIG. 3A
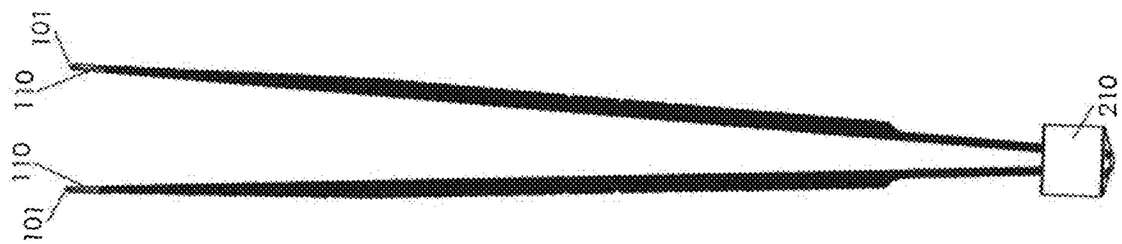

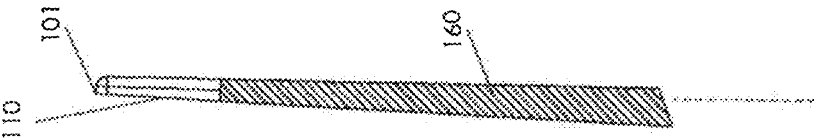
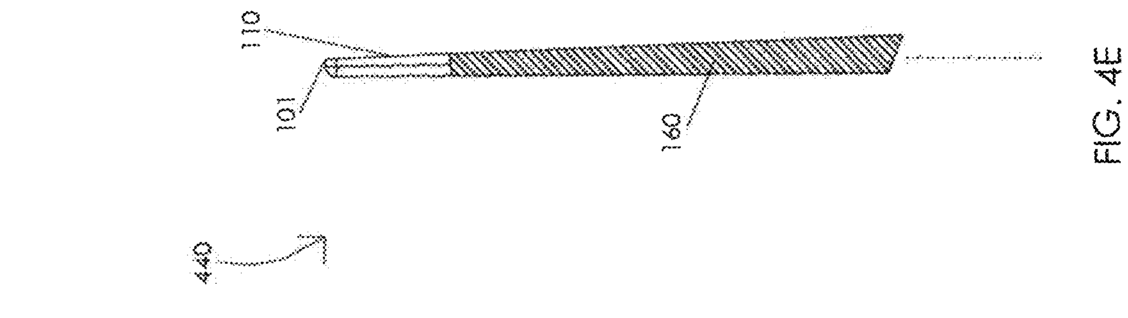
FIG. 4E

160
160
560
110
110
602
600
101
101
500

| | Aluminum 6061-T6 | Zirconium Copper C15000 |
|---|---|---|
| Density | 2.7 $\frac{g}{cm^3}$ | 8.89 $\frac{g}{cm^3}$ |
| Ultimate Tensile Strength | 310 MPa | 430 MPa |
| Yield Tensile Strength | 276 MPa | 415 MPa |
| Elongation at Break | 12% | 15% |
| Modulus of Elasticity | 68.9 GPa | 129 GPa |
| Poisson's Ratio | 0.33 | 0.34 |
| Shear Modulus | 26 GPa | 43 GPa |
| Shear Strength | 207 MPa | 280 MPa |
| Electrical Conductivity | 43% IACS | 93% IACS |
| Thermal Conductivity | 167 $\frac{W}{m\,K}$ | 370 $\frac{W}{m\,K}$ |
| Specific Heat Capacity | 0.214 $\frac{BTU}{lb\,°F}$ | 0.092 $\frac{BTU}{lb\,°F}$ |

Figure 7

| | | Thermal Potential (W*m^2)/K | | | % Copper Better than Aluminum | |
|---|---|---|---|---|---|---|
| | | Handle | Bayonet | | Handle | Bayonet |
| *Copper* | *7"* | 0.00085845 | 0.000146 | | 146.3904 | 135.1767 |
| | | 0.000872893 | 0.00016 | | 146.3704 | 135.831 |
| | | 0.000879738 | 0.000167 | | 147.1377 | 139.6295 |
| | *8"* | 0.000966593 | 0.000245 | | 144.5394 | 133.8043 |
| | | 0.000981242 | 0.00026 | | 144.6213 | 134.6355 |
| | | 0.000990185 | 0.000269 | | 145.6125 | 138.0898 |
| | *9"* | 0.001115226 | 0.000385 | | 146.7944 | 142.6675 |
| | | 0.001130118 | 0.0004 | | 146.8748 | 143.1217 |
| | | 0.001141268 | 0.000411 | | 148.0314 | 146.2957 |
| | *Lawton* | 0.000866436 | 8.83E-05 | | 202.0387 | 128.2479 |
| ***Aluminum*** | *7"* | 0.000586412 | 0.000108 | AVG W/ Lawton | 151.8411 | 137.75 |
| | | 0.000596359 | 0.000118 | AVG W/O | 146.2636 | 138.8059 |
| | | 0.000597902 | 0.00012 | | | |
| | *8"* | 0.00066874 | 0.000183 | | | |
| | | 0.000678491 | 0.000193 | | | |
| | | 0.000680014 | 0.000195 | | | |
| | *9"* | 0.00075972 | 0.00027 | | | |
| | | 0.000769443 | 0.000279 | | | |
| | | 0.000770963 | 0.000281 | | | |
| | *Lawton* | 0.000428846 | 6.89E-05 | | | |

Figure 8

| | | | Electrical Conductivity (%IACS*m^3) | | | % Copper Better than Aluminum | |
|---|---|---|---|---|---|---|---|
| | | | Handle | Bayonet | | Handle | Bayonet |
| *Copper* | *7"* | *0.5mm* | 2.08812E-06 | 3.55E-07 | | 138.2105 | 127.6235 |
| | | *1.0mm* | 2.12325E-06 | 3.9E-07 | | 138.1917 | 128.2412 |
| | | *1.5mm* | 2.1399E-06 | 4.06E-07 | | 138.9161 | 131.8275 |
| | *8"* | *0.5mm* | 2.35117E-06 | 5.97E-07 | | 136.463 | 126.3277 |
| | | *1.0mm* | 2.38681E-06 | 6.33E-07 | | 136.5403 | 127.1125 |
| | | *1.5mm* | 2.40856E-06 | 6.54E-07 | | 137.4761 | 130.3738 |
| | *9"* | *0.5mm* | 2.71271E-06 | 9.36E-07 | | 138.592 | 134.6957 |
| | | *1.0mm* | 2.74893E-06 | 9.73E-07 | | 138.6679 | 135.1245 |
| | | *1.5mm* | 2.77606E-06 | 1E-06 | | 139.7599 | 138.1212 |
| | *Lawton* | *0.5mm* | 2.10755E-06 | 2.15E-07 | | 190.7494 | 121.0819 |
| *Aluminum* | *7"* | *0.5mm* | 1.51083E-06 | 2.78E-07 | AVG W/ Lawton | 143.3567 | 130.0529 |
| | | *1.0mm* | 1.53646E-06 | 3.04E-07 | AVG W/O | 138.0908 | 131.0497 |
| | | *1.5mm* | 1.54043E-06 | 3.08E-07 | | | |
| | *8"* | *0.5mm* | 1.72294E-06 | 4.73E-07 | | | |
| | | *1.0mm* | 1.74806E-06 | 4.98E-07 | | | |
| | | *1.5mm* | 1.75198E-06 | 5.02E-07 | | | |
| | *9"* | *0.5mm* | 1.95734E-06 | 6.95E-07 | | | |
| | | *1.0mm* | 1.98239E-06 | 7.2E-07 | | | |
| | | *1.5mm* | 1.9863E-06 | 7.24E-07 | | | |
| | *Lawton* | *0.5mm* | 1.10488E-06 | 1.77E-07 | | | |

Figure 9

| | | | Volume of | | | | % Copper Better than Aluminum | | | |
|---|---|---|---|---|---|---|---|---|---|---|
| | | | Handle (in^3) | Bayonet (in^3) (4.5" from end of | Handle (m^3) | Bayonet (m^3) | Handle | Bayonet | | |
| Copper | 7" | 0.5mm | 0.141584 | 0.024086 | 2.32014E-06 | 3.94697E-07 | 66.0339255 | 60.9756715 | | |
| | | 1.0mm | 0.143966 | 0.026431 | 2.35917E-06 | 4.33125E-07 | 66.02491195 | 61.27080532 | | |
| | | 1.5mm | 0.145095 | 0.027526 | 2.37767E-06 | 4.51068E-07 | 66.37101349 | 62.98473449 | | |
| | 8" | 0.5mm | 0.15942 | 0.040489 | 2.61241E-06 | 6.63493E-07 | 65.19898737 | 60.3565732 | | |
| | | 1.0mm | 0.161836 | 0.042905 | 2.65201E-06 | 7.03084E-07 | 65.23593336 | 60.73152434 | | |
| | | 1.5mm | 0.163311 | 0.044354 | 2.67618E-06 | 7.26829E-07 | 65.68302934 | 62.28969469 | | |
| | 9" | 0.5mm | 0.183934 | 0.063444 | 3.01413E-06 | 1.03966E-06 | 66.21618703 | 64.35461784 | | |
| | | 1.0mm | 0.18639 | 0.065943 | 3.05437E-06 | 1.08061E-06 | 66.25244817 | 64.55949013 | | |
| | | 1.5mm | 0.188229 | 0.067773 | 3.08451E-06 | 1.1106E-06 | 66.77415578 | 65.99123661 | | |
| | Lowton | 0.5mm | 0.142901 | 0.014569 | 2.34172E-06 | 2.38742E-07 | 91.13584184 | 57.89022236 | | |
| Aluminum | 7" | 0.5mm | 0.214411 | 0.039501 | 3.51355E-06 | 6.47303E-07 | | AVG W/ Lawton | 68.49264343 | 62.13640705 |
| | | 1.0mm | 0.218048 | 0.043138 | 3.57315E-06 | 7.06902E-07 | | AVG W/O | 65.9767325 | 62.61264979 |
| | | 1.5mm | 0.218612 | 0.043703 | 3.58239E-06 | 7.16161E-07 | | | | |
| | 8" | 0.5mm | 0.244513 | 0.067083 | 4.00683E-06 | 1.09929E-06 | | | | |
| | | 1.0mm | 0.248078 | 0.070647 | 4.06525E-06 | 1.15769E-06 | | | | |
| | | 1.5mm | 0.248635 | 0.071206 | 4.07438E-06 | 1.16685E-06 | | | | |
| | 9" | 0.5mm | 0.277778 | 0.098585 | 4.55195E-06 | 1.61551E-06 | | | | |
| | | 1.0mm | 0.281333 | 0.102143 | 4.6102E-06 | 1.67382E-06 | | | | |
| | | 1.5mm | 0.281889 | 0.1027 | 4.61931E-06 | 1.68294E-06 | | | | |
| | Lowton | 0.5mm | 0.1568 | 0.025184 | 2.56948E-06 | 4.1269E-07 | | | | |

BIPOLAR FORCEPS

CROSS REFERENCE TO RELATED APPLICATIONS

This application is a continuation-in-part of U.S. application Ser. No. 16/284,324 filed 25 Feb. 2019, which is a continuation-in-part of U.S. application Ser. No. 15/697,930 filed 7 Sep. 2017, (now abandoned), which is a continuation of U.S. application Ser. No. 15/242,696, filed 22 Aug. 2016 (now U.S. Pat. No. 9,801,680, issued 11 Oct. 2017), which is a continuation of U.S. application Ser. No. 14/694,695, filed 23 Apr. 2015 (now U.S. Pat. No. 9,452,012, issued 7 Sep. 2016), which is a continuation of U.S. application Ser. No. 13/742,120, filed 15 Jan. 2013 (now U.S. Pat. No. 9,044,242, issued 2 Jun. 2015), the entire disclosure of each are incorporated herein by reference in their entirety.

STATEMENT REGARDING FEDERALLY SPONSORED RESEARCH & DEVELOPMENT

Not applicable.

BACKGROUND OF THE INVENTION

The present disclosure relates to a surgical instrument, and, more particularly, to a bipolar forceps for electrosurgery.

A variety of surgical procedures may be performed using electrosurgery with a bipolar forceps, including, but not limited to, neurosurgical, spinal, dermatological, gynecological, cardiac, plastic, ocular, maxillofacial, orthopedic, urological, and general surgical procedures. Generally, electrosurgery is performed by applying a high-frequency electrical current to a targeted area of biological tissue to cut or coagulate the tissue. Typically, a bipolar forceps includes an active electrode and a return electrode operatively connected to a power source of high-frequency electrical current. In operation, the high-frequency electrical current flows out from the active electrode, through the targeted area of biological tissue, and into the return electrode. The flow of high-electrical current through the targeted area of biological tissue cuts and/or coagulates the tissue. During this process, thermal energy, such as heat, is created at the point of application, such as the targeted area of biological tissue, and then transferred to the arms or tips of the bipolar forceps. In particular, repeated or extended use of the bipolar forceps can result in increased thermal energy which often results in the bipolar forceps charring or sticking to biological tissue. When bipolar forceps stick to cauterized tissue, surgeons must spend time separating the tips from the tissue, which can result in rebleeding of the cauterized tissue. In addition, the thermal energy may undesirably damage or char non-targeted biological tissue in proximity to the targeted area of biological tissue. During operation, surgeons may rely on visual cues to indicate the amount and degree of damage to biological tissue. For example, it is preferable to see a visual indication of "white" coagulation, which indicates decreased tissue damage, as opposed to "black" coagulation, which indicates increased tissue damage.

Typically, bipolar forceps include non-stick materials covering the electrodes to reduce the tendency of sticking to biological tissue. However, even the use of such non-stick materials does not completely prevent the sticking and charring of biological tissue, especially during procedures that require extended and repeated use. In such procedures, conventional bipolar forceps are not capable of transferring thermal energy away from the electrodes at a sufficient rate to prevent the electrodes from heating up and reaching a threshold of thermal energy that causes sticking and charring of biological tissue. In addition, the application of non-stick materials to the bipolar forceps increases cost and time of manufacturing. For example, the process of applying non-stick materials typically involves multiple steps of plating multiple materials. Cost is an important design criteria in the manufacture of bipolar forceps, and in particular for the manufacture of disposable bipolar forceps.

Therefore, there is a need for a cost-effective bipolar forceps with a high thermal transfer rate to prevent damage to biological tissue during electrosurgery.

BRIEF DESCRIPTION OF THE INVENTION

The present disclosure presents a bipolar forceps. Illustratively, a bipolar forceps may comprise a first forceps arm having a first forceps arm aperture, a first forceps jaw, and a first forceps arm conductor tip; a second forceps arm having a first forceps arm aperture, a second forceps jaw, and a second forceps arm conductor tip; and an input conductor isolation mechanism having a first forceps arm housing and a second forceps arm housing. In one or more embodiments, the first forceps arm may be disposed in the first forceps arm housing and the second forceps arm may be disposed in the second forceps arm housing. Illustratively, an application of a force to a lateral portion of the forceps arms may be configured to close the forceps jaws. In one or more embodiments, a reduction of a force applied to a lateral portion of the forceps arms may be configured to open the forceps jaws.

In one embodiment a surgical instrument for electrosurgery includes a first forceps arm having a first forceps arm distal end and a first forceps arm proximal end, a first forceps jaw of the first forceps arm having a first forceps jaw distal end and a first forceps jaw proximal end wherein the first forceps jaw distal end is the first forceps arm distal end, a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, a second forceps arm having a second forceps arm distal end and a second forceps arm proximal end, the second forceps arm disposed opposite the first forceps arm, a second forceps jaw of the second forceps arm having a second forceps jaw distal end and a second forceps jaw proximal end, the second forceps jaw disposed opposite the first forceps jaw wherein the second forceps jaw distal end is the second forceps arm distal end, a second conductor tip of the second forceps arm having a second conductor tip distal end and a second conductor tip proximal end, and the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end. The first forceps arm and the second forceps arm are configured to transfer thermal energy away from the first conductor tip and second conductor tip at a rate sufficient to maintain the temperature of the first conductor tip and second conductor tip s below a designated temperature. The first and second forceps arms being composed of a zirconium copper alloy.

In another embodiment, a surgical instrument for electrosurgery includes a first forceps arm having a first forceps arm distal end and a first forceps arm proximal end, a first forceps jaw of the first forceps arm having a first forceps jaw distal end and a first forceps jaw proximal end wherein the first forceps jaw distal end is the first forceps arm distal end, a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, the first conductor tip having a first plating layer deposited directly to at least a portion of an outer surface of the first conductor tip, a second forceps arm having a second forceps arm distal end and a second forceps arm proximal end, the second forceps arm disposed opposite the first forceps arm, a second forceps jaw of the second forceps arm having a second forceps jaw distal end and a second forceps jaw proximal end, the second forceps jaw disposed opposite the first forceps jaw wherein the second forceps jaw distal end is the second forceps arm distal end, a second conductor tip of the second forceps arm having a second conductor tip distal end and a second conductor tip proximal end, and the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end, the second conductor tip having a second plating layer deposited directly to at least a portion of an outer surface of the second conductor tip. The first forceps arm and the second forceps arm are configured to transfer thermal energy away from the first conductor tip and second conductor tip at a rate sufficient to maintain the temperature of the first conductor tip and second conductor tip s below a designated temperature. The first and second forceps arms being composed of a zirconium copper alloy.

In another embodiment, a method of manufacturing a surgical instrument includes providing a first forceps arm having a first forceps arm distal end and a first forceps arm proximal end, providing a first forceps jaw of the first forceps arm having a first forceps jaw distal end and a first forceps jaw proximal end wherein the first forceps jaw distal end is the first forceps arm distal end, providing a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, providing a second forceps arm having a second forceps arm distal end and a second forceps arm proximal end, the second forceps arm disposed opposite the first forceps arm, providing a second forceps jaw of the second forceps arm having a second forceps jaw distal end and a second forceps jaw proximal end, the second forceps jaw disposed opposite the first forceps jaw wherein the second forceps jaw distal end is the second forceps arm distal end, providing a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end, depositing a first plating layer directly onto at least a portion of an a first outer surface of the first conductor tip, and depositing a second plating layer directly onto at least a portion of a second outer surface of the second conductor tip. The first forceps arm and the second forceps arm are configured to transfer thermal energy away from the first conductor tip and second conductor tip at a rate sufficient to maintain the temperature of the first conductor tip and second conductor tip s below a designated temperature. The first and second forceps arms being composed of a zirconium copper alloy.

BRIEF DESCRIPTION OF THE DRAWINGS

The present inventive subject matter will be better understood from reading the following description of non-limiting embodiments, with reference to the attached drawings, wherein below:

FIGS. 3A, 3B, 3C, 3D, and 3E are schematic diagrams illustrating a gradual closing of a bipolar forceps;

FIGS. 4A, 4B, 4C, 4D, and 4E are schematic diagrams illustrating a gradual opening of a bipolar forceps;

FIG. 7 is a table comparing properties of an aluminum alloy typical of conventional forceps arm and a zirconium copper alloy for embodiments of the forceps arm.

FIG. 8 is a table showing thermal potential of the zirconium copper alloy in various embodiments of the forceps arm compared to identical size/shape aluminum embodiments.

FIG. 9 is a table showing electrical conductivity of the zirconium copper alloy in various embodiments of the forceps arm compared to identical size/shape aluminum embodiments.

FIG. 10 is a table showing a volumetric comparison between zirconium copper alloy and aluminum alloy forceps embodiments.

Corresponding reference numerals indicate corresponding parts throughout the several figures of the drawings.

DETAILED DESCRIPTION OF THE INVENTION

Figure 1:
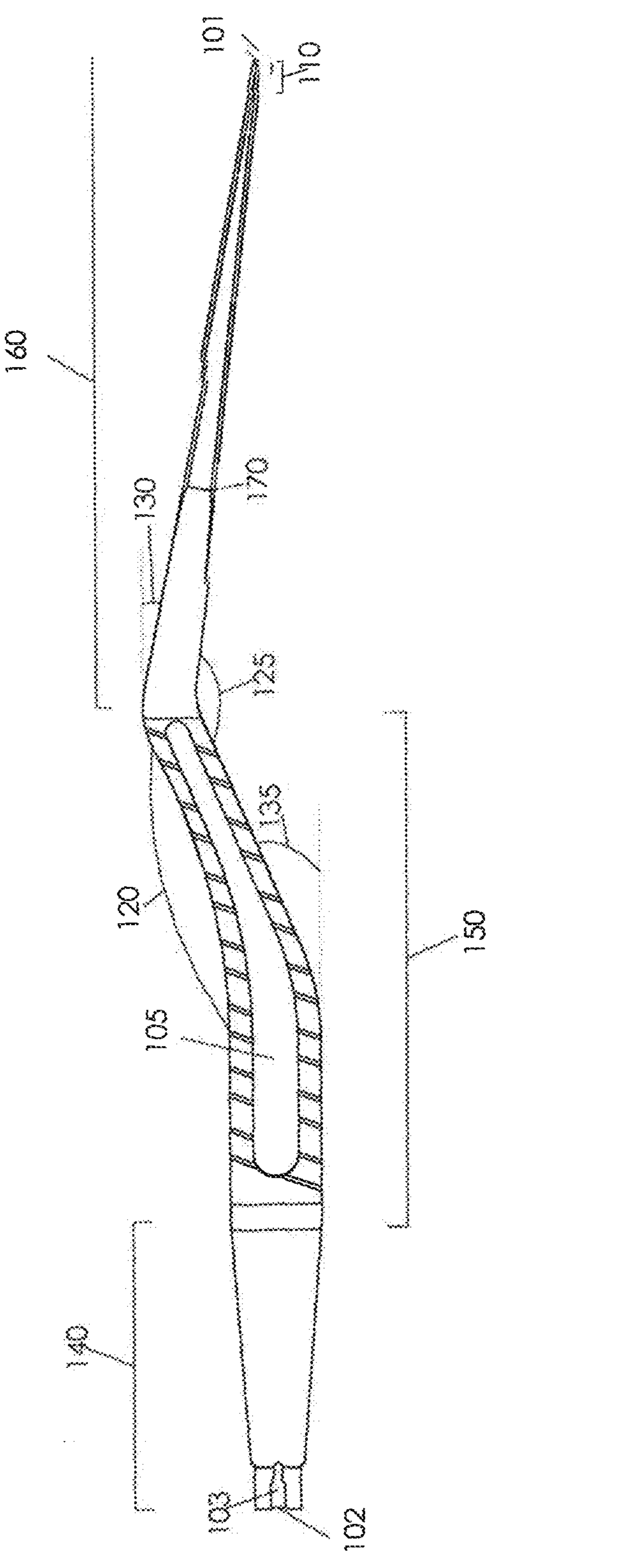
FIG. 1 is a schematic diagram illustrating a side view of a forceps arm.

The following detailed description illustrates the inventive subject matter by way of example and not by way of limitation. The description enables one of ordinary skill in the art to make and use the inventive subject matter, describes several embodiments of the inventive subject matter, as well as adaptations, variations, alternatives, and uses of the inventive subject matter. Additionally, it is to be understood that the inventive subject matter is not limited in its application to the details of construction and the arrangements of components set forth in the following description or illustrated in the drawings. The inventive subject matter is capable of other embodiments and of being practiced or being carried out in various ways. Also, it is to be understood that the phraseology and terminology used herein is for the purpose of description and should not be regarded as limiting on all embodiments of the inventive subject matter.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

FIG. 1 is a schematic diagram illustrating a side view of a forceps arm 100. Illustratively, a forceps arm 100 may comprise an input conductor housing 103, a forceps arm aperture 105, a conductor tip 110, a forceps arm superior incline angle 120, a forceps arm inferior decline angle 125, a forceps arm superior decline angle 130, a forceps arm inferior incline angle 135, a socket interface 140, a forceps arm grip 150, a forceps jaw 160, and a forceps jaw taper interface 170. In one or more embodiments, forceps arm 100 may be composed of any suitable material, e.g., polymers, metals, metal alloys, etc., or from any combination of suitable materials. Illustratively, forceps arm 100 may be manufactured from an electrically conductive material, e.g., metal, graphite, conductive polymers, etc. In one or more embodiments, forceps arm 100 may be manufactured from an electrically conductive metal, e.g., silver, copper, gold, aluminum, etc. Illustratively, forceps arm 100 may be manufactured from an electrically conductive metal alloy, e.g., a silver alloy, a copper alloy, a gold alloy, an aluminum alloy, stainless steel, etc. In an exemplary embodiment, the forceps arm 100 is composed of a zirconium copper alloy. For example, the forceps arm 100 may be manufactured from zirconium and copper materials or a zirconium copper alloy material. In an exemplary embodiment, the zirconium copper alloy forceps arm 100 has high thermal and electrical conductivity, such as when compared to a conventional forceps arm manufactured from an aluminum or stainless steel material. The zirconium copper alloy forceps arm 100 is characterized by high resistance to softening and resistance to deformation at high temperature, particularly when compared to pure copper.

In one or more embodiments, forceps arm 100 may be manufactured from a material having an electrical conductivity in a range of 30.0×106 to Siemens per meter at a temperature of 20.0° C., e.g., forceps arm 100 may be manufactured from a material having an electrical conductivity of 35.5×106 Siemens per meter at a temperature of 20.0° C. Illustratively, forceps arm 100 may be manufactured from a material having an electrical conductivity of less than 30.0×106 Siemens per meter or greater than 40.0×106 Siemens per meter at a temperature of 20.0° C. In one or more embodiments, forceps arm 100 may be manufactured from a material having a thermal conductivity in a range of 180.0 to 250.0 Watts per meter Kelvin at a temperature of 20.0° C., e.g., forceps arm 100 may be manufactured from a material having a thermal conductivity of 204.0 Watts per meter Kelvin at a temperature of 20.0° C. Illustratively, forceps arm 100 may be manufactured from a material having a thermal conductivity of less than 180.0 Watts per meter Kelvin or greater than 250.0 Watts per meter Kelvin at a temperature of 20.0° C. In one or more embodiments, forceps arm 100 may be manufactured from a material having an electrical conductivity in a range of 30.0×106 to Siemens per meter and a thermal conductivity in a range of 180.0 to 250.0 Watts per meter Kelvin at a temperature of 20.0° C., e.g., forceps arm 100 may be manufactured from a material having an electrical conductivity of 35.5×106 Siemens per meter and a thermal conductivity of 204.0 Watts per meter Kelvin at a temperature of 20.0° C.

Illustratively, forceps arm 100 may have a density in a range of 0.025 to 0.045 pounds per cubic inch, e.g., forceps arm 100 may have a density of 0.036 pounds per cubic inch. In one or more embodiments, forceps arm 100 may have a density less than 0.025 pounds per cubic inch or greater than 0.045 pounds per cubic inch. For example, forceps arm 100 may have a density of 0.0975 pounds per cubic inch. Illustratively, forceps arm 100 may have a mass in a range of 0.01 to 0.025 pounds, e.g., forceps arm 100 may have a mass of 0.017 pounds. In one or more embodiments, forceps arm 100 may have a mass less than 0.01 pounds or greater than 0.025 pounds. Illustratively, forceps arm 100 may have a volume in a range of 0.12 to 0.23 cubic inches, e.g., forceps arm 100 may have a volume of 0.177 cubic inches. In one or more embodiments, forceps arm 100 may have a volume less than 0.12 cubic inches or greater than 0.23 cubic inches. Illustratively, forceps arm aperture 105 may be configured to reduce a stiffness of forceps arm 100. In one or more embodiments, forceps arm aperture 105 may be configured to increase a flexibility of forceps arm 100.

Illustratively, forceps arm aperture 105 may be configured to reduce a mass of forceps arm 100. In one or more embodiments, forceps arm aperture 105 may be configured to reduce a mass of forceps arm 100 by an avoided mass in a range of 0.005 to 0.012 pounds, e.g., forceps arm aperture 105 may be configured to reduce a mass of forceps arm 100 by an avoided mass of 0.00975 pounds. Illustratively, forceps arm aperture 105 may be configured to reduce a mass of forceps arm 100 by an avoided mass less than 0.005 pounds or greater than 0.012 pounds. In one or more embodiments, forceps arm aperture 105 may have an aperture area in a range of 0.3 to 0.65 square inches, e.g., forceps arm aperture 105 may have an aperture area of 0.485 square inches. Illustratively, forceps arm aperture 105 may have an aperture area less than 0.3 square inches or greater than 0.65 square inches. In one or more embodiments, forceps arm aperture 105 may have an aperture perimeter length in a range of 4.0 to 7.0 inches, e.g., forceps arm aperture 105 may have an aperture perimeter length of 5.43 inches. Illustratively, forceps arm aperture 105 may have an aperture perimeter length less than 4.0 inches or greater than 7.0 inches.

In one or more embodiments, forceps arm aperture 105 may be configured to decrease a thermal conductivity of forceps arm grip 150. Illustratively, forceps arm aperture 105 may be configured to decrease an electrical conductivity of forceps arm grip 150. In one or more embodiments, forceps arm aperture 105 may be configured to decrease a thermal conductivity and to decrease an electrical conductivity of forceps arm grip 150. Illustratively, forceps arm aperture 105 may be configured to reduce a probability that forceps arm grip 150 may reach a temperature of 48.89° C. during a surgical procedure. In one or more embodiments, forceps arm aperture 105 may be configured to reduce a probability that forceps arm grip 150 may reach a temperature of 48.89° C. during a surgical procedure, e.g., by decreasing a thermal conductivity of forceps arm grip 150. Illustratively, forceps arm aperture 105 may be configured to reduce a probability that forceps arm grip 150 may reach a temperature of 48.89° C. during a surgical procedure, e.g., by decreasing an electrical conductivity of forceps arm grip 150. In one or more embodiments, forceps arm aperture 105 may be configured to reduce a probability that forceps arm grip 150 may reach a temperature of 48.89° C. during a surgical procedure, e.g., by decreasing a thermal conductivity and an electrical conductivity of forceps arm grip 150.

Illustratively, forceps arm 100 may have a surface area in a range of 4.5 to 7.5 square inches, e.g., forceps arm 100 may have a surface area of 6.045 square inches. In one or more embodiments, forceps arm 100 may have a surface area less than 4.5 square inches or greater than 7.5 square inches. Illustratively, conductor tip 110 may have a surface area in a range of 0.02 to 0.05 square inches, e.g., conductor tip 110 may have a surface area of 0.035 square inches. In one or more embodiments, conductor tip 110 may have a surface area less than 0.02 square inches or greater than 0.05 square inches. Illustratively, a ratio of forceps arm 100 surface area to conductor tip 110 surface area may be in a range of 150.0 to 225.0, e.g., a ratio of forceps arm 100 surface area to conductor tip 110 surface area may be 172.7. In one or more embodiments, a ratio of forceps arm 100 surface area to conductor tip 110 surface area may be less than 150.0 or greater than 225.0.

Illustratively, conductor tip 110 may be configured to prevent tissue from sticking to conductor tip 110. In one or more embodiments, conductor tip 110 may comprise a evenly polished material configured to prevent tissue sticking. Illustratively, conductor tip 110 may have a length in a range of 0.22 to 0.3 inches, e.g., conductor tip 110 may have a length of 0.26 inches. In one or more embodiments, conductor tip 110 may have a length less than 0.22 inches or greater than 0.3 inches. Illustratively, conductor tip 110 may have a width in a range of 0.03 to 0.05 inches, e.g., conductor tip 110 may have a width of 0.04 inches. In one or more embodiments, conductor tip 110 may have a width less than 0.03 inches or greater than 0.05 inches. Illustratively, a geometry of forceps jaw 160 may comprise a tapered portion, e.g., a tapered portion from forceps jaw taper interface 170 to forceps arm distal end 101. In one or more embodiments, forceps jaw 160 may comprise a tapered portion having a tapered angle in a range of 3.0 to 4.5 degrees, e.g., forceps jaw 160 may comprise a tapered portion having a tapered angle of 3.72 degrees. Illustratively, forceps jaw 160 may comprise a tapered portion having a tapered angle of less than 3.0 degrees or greater than 4.5 degrees.

Illustratively, forceps arm 100 may comprise a material having a modulus of elasticity in a range of 9.0×106 to 11.0×106 pounds per square inch, e.g., forceps arm 100 may comprise a material having a modulus of elasticity of 10.0×106 pounds per square inch. In one or more embodiments, forceps arm 100 may comprise a material having a modulus of elasticity less than 9.0×106 pounds per square inch or greater than 11.0×106 pounds per square inch. Illustratively, forceps arm 100 may comprise a material having a shear modulus in a range of 3.5×106 to 4.5×106 pounds per square inch, e.g., forceps arm 100 may comprise a material having a shear modulus of 3.77×106 pounds per square inch. In one or more embodiments, forceps arm 100 may comprise a material having a shear modulus less than 3.5×106 pounds per square inch or greater than 4.5×106 pounds per square inch.

Illustratively, forceps arm superior incline angle 120 may comprise any angle greater than 90.0 degrees. In one or more embodiments, forceps arm superior incline angle 120 may comprise any angle in a range of 150.0 to 170.0 degrees, e.g., forceps arm superior incline angle 120 may comprise a 160.31 degree angle. Illustratively, forceps arm superior incline angle 120 may comprise an angle less than 150.0 degrees or greater than 170.0 degrees. In one or more embodiments, forceps arm inferior decline angle 125 may comprise any angle greater than 90.0 degrees. Illustratively, forceps arm inferior decline angle 125 may comprise any angle in a range of 140.0 to 160.0 degrees, e.g., forceps arm inferior decline angle 125 may comprise a 149.56 degree angle. In one or more embodiments, forceps arm inferior decline angle 125 may comprise an angle less than 140.0 degrees or greater than 160.0 degrees. Illustratively, forceps arm inferior decline angle 125 may comprise any angle less than forceps arm superior incline angle 120, e.g., forceps arm inferior decline angle 125 may comprise an angle in a range of 5.0 to 15.0 degrees less than forceps arm superior incline angle 120. In one or more embodiments, forceps arm inferior decline angle 125 may comprise an angle less than 5.0 degrees or greater than 15.0 degrees less than forceps arm superior incline angle 120.

Illustratively, forceps arm superior decline angle 130 may comprise any angle less than 90.0 degrees. In one or more embodiments, forceps arm superior decline angle 130 may comprise any angle in a range of 5.0 to 15.0 degrees, e.g., forceps arm superior decline angle 130 may comprise an 11.3 degree angle. Illustratively, forceps arm superior decline angle 130 may comprise an angle less than 5.0 degrees or greater than 15.0 degrees. In one or more embodiments, forceps arm inferior incline angle 135 may comprise any angle less than 90.0 degrees. Illustratively, forceps arm inferior incline angle 135 may comprise any angle in a range of 15.0 to 30.0 degrees, e.g., forceps arm inferior incline angle 135 may comprise a 23.08 degree angle. In one or more embodiments, forceps arm inferior incline angle 135 may comprise an angle less than 15.0 degrees or greater than 30.0 degrees. Illustratively, forceps arm inferior incline angle 135 may comprise any angle greater than forceps arm superior decline angle 130, e.g., forceps arm inferior incline angle 135 may comprise an angle in a range of 5.0 to 15.0 degrees greater than forceps arm superior decline angle 130. In one or more embodiments, forceps arm inferior incline angle 135 may comprise an angle less than 5.0 degrees or greater than 15.0 degrees greater than forceps arm superior decline angle 130.

Figure 2:
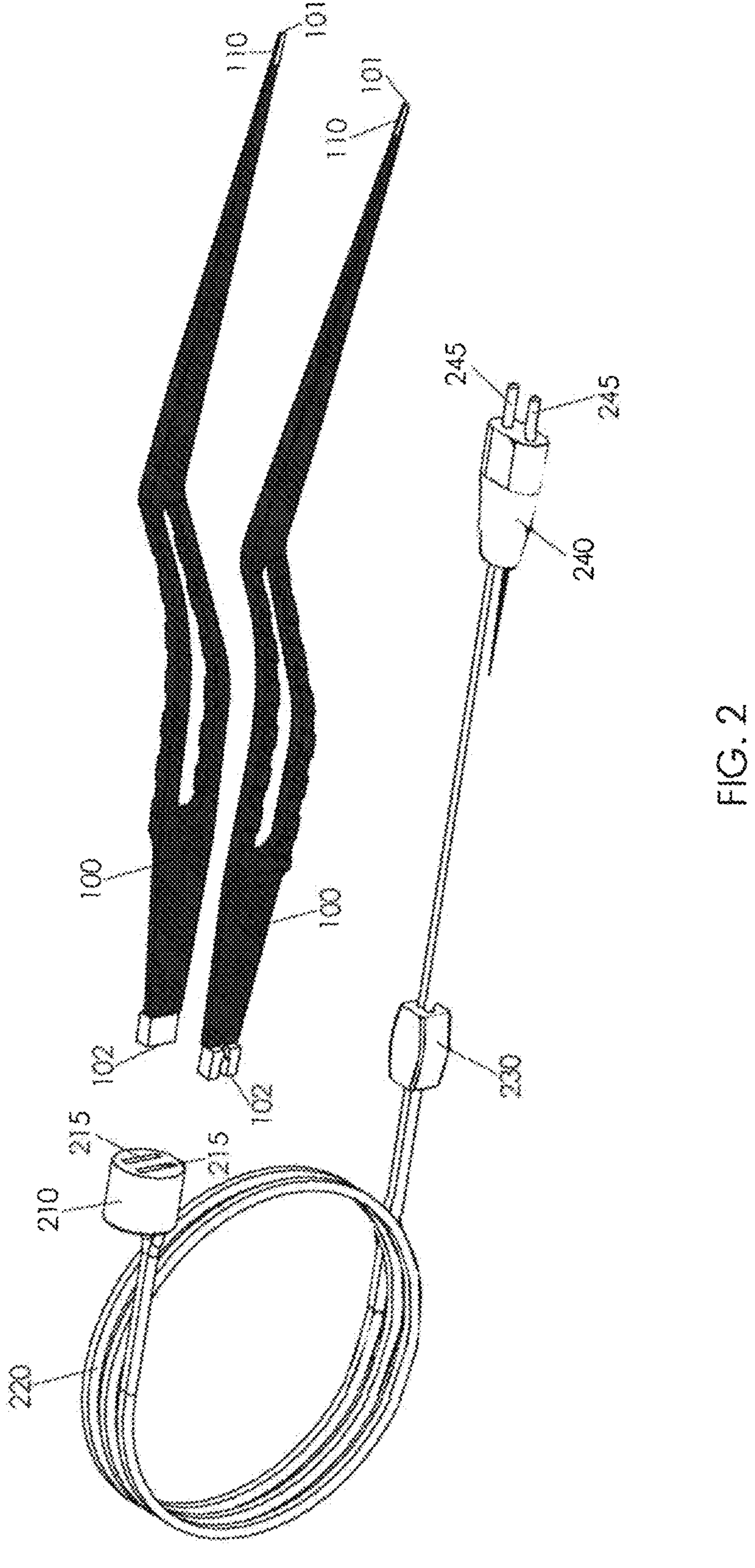
FIG. 2 is a schematic diagram illustrating an exploded view of a bipolar forceps assembly.

FIG. 2 is a schematic diagram illustrating an exploded view of a bipolar forceps assembly 200. In one or more embodiments, a bipolar forceps assembly 200 may comprise a pair of forceps arms 100, an input conductor isolation mechanism 210, a bipolar cord 220, a bipolar cord separation control 230, and an electrosurgical generator adaptor 240. Illustratively, a portion of each forceps arm 100 may be coated with a material having a high electrical resistivity, e.g., a portion of each forceps arm 100 may be coated with an electrical insulator material. In one or more embodiments, input conductor housings 103 and conductor tips 110 may not be coated with a material, e.g., input conductor housings 103 and conductor tips 110 may comprise electrical leads. Illustratively, a portion of each forceps arm 100 may be coated with a thermoplastic material, e.g., a portion of each forceps arm 100 may be coated with nylon. In one or more embodiments, a portion of each forceps arm 100 may be coated with a fluoropolymer, e.g., a portion of each forceps arm 100 may be coated with polyvinylidene fluoride. Illustratively, a portion of each forceps arm 100 may be coated with a material having an electrical conductivity less than 1.0×10−8 Siemens per meter at a temperature of 20.0° C., e.g., a portion of each forceps arm 100 may be coated with a material having an electrical conductivity of 1.0×10−12 Siemens per meter at a temperature of 20.0° C. In one or more embodiments, a portion of each forceps arm 100 may be coated with a material having a thermal conductivity of less than 1.0 Watts per meter Kelvin at a temperature of 20.0° C., e.g., a portion of each forceps arm 100 may be coated with a material having a thermal conductivity of 0.25 Watts per meter Kelvin at a temperature of 20.0° C. Illustratively, a portion of each forceps arm 100 may be coated with a material having an electrical conductivity of less than 1.0×10−8 Siemens per meter and a thermal conductivity of less than 1.0 Watts per meter Kelvin at a temperature of 20.0° C., e.g., a portion of each forceps arm 100 may be coated with a material having an electrical conductivity of 1.0×10−12 Siemens per meter and a thermal conductivity of 0.25 Watts per meter Kelvin at a temperature of 20.0° C. In one or more embodiments, a portion of each forceps arm 100 may be coated with a material wherein a coating thickness of the material is in a range of 0.005 to 0.008 inches, e.g., a portion of each forceps arm 100 may be coated with a material wherein a coating thickness of the material is 0.0065 inches. Illustratively, a portion of each forceps arm 100 may be coated with a material wherein a coating thickness of the material is less than 0.005 inches or greater than 0.008 inches. In one or more embodiments, a portion of each forceps arm 100 may be coated with a material having an electrical conductivity of less than 1.0×10−8 Siemens per meter and a thermal conductivity of less than 1.0 Watts per meter Kelvin at a temperature of 20.0° C. wherein a coating thickness of the material is in a range of 0.005 to 0.008 inches, e.g., a portion of each forceps arm 100 may be coated with a material having an electrical conductivity of 1.0×10−12 Siemens per meter and a thermal conductivity of 0.25 Watts per meter Kelvin at a temperature of 20.0° C. wherein a coating thickness of the material is 0.0065 inches. Illustratively, a portion of each forceps arm 100 may be coated with a material having a material mass in a range of 0.0015 to 0.0025 pounds, e.g., a portion of each forceps arm 100 may be coated with a material having a material mass of 0.0021 pounds. In one or more embodiments, a portion of each forceps arm 100 may be coated with a material having a material mass less than 0.0015 pounds or greater than 0.0025 pounds.

Illustratively, input conductor isolation mechanism 210 may comprise a first forceps arm housing 215 and a second forceps arm housing 215. In one or more embodiments, input conductor isolation mechanism 210 may be configured to separate a first bipolar input conductor and a second bipolar input conductor, e.g., input conductor isolation mechanism 210 comprise a material with an electrical resistivity greater than 1×1016 ohm meters. Illustratively, input conductor isolation mechanism 210 may comprise a material with an electrical resistivity less than or equal to 1×1016 ohm meters. In one or more embodiments, input conductor isolation mechanism 210 may comprise an interface between bipolar cord 220 and forceps arms 100. Illustratively, a first bipolar input conductor and a second bipolar input conductor may be disposed within bipolar cord 220, e.g., bipolar cord 220 may be configured to separate the first bipolar input conductor and the second bipolar input conductor. In one or more embodiments, a first bipolar input conductor may be electrically connected to first forceps arm 100, e.g., the first bipolar input conductor may be disposed within input conductor housing 103. Illustratively, a second bipolar input conductor may be electrically connected to second forceps arm 100, e.g., the second bipolar input conductor may be disposed within input conductor housing 103. In one or more embodiments, a portion of first forceps arm 100 may be disposed within first forceps arm housing 215, e.g., first forceps arm proximal end 102 may be disposed within first forceps arm housing 215. Illustratively, first forceps arm 100 may be fixed within first forceps arm housing 215, e.g., by an adhesive or any suitable fixation means. In one or more embodiments, a first bipolar input conductor may be disposed within first forceps arm housing 215, e.g., the first bipolar input conductor may be electrically connected to first forceps arm 100. Illustratively, a first bipolar input conductor may be fixed within first forceps arm housing 215 wherein the first bipolar input conductor is electrically connected to first forceps arm 100. In one or more embodiments, a portion of second forceps arm 100 may be disposed within second forceps arm housing 215, e.g., second forceps arm proximal end 102 may be disposed within second forceps arm housing 215. Illustratively, second forceps arm 100 may be fixed within second forceps arm housing 215, e.g., by an adhesive or any suitable fixation means. In one or more embodiments, a second bipolar input conductor may be disposed within second forceps arm housing 215, e.g., the second bipolar input conductor may be electrically connected to second forceps arm 100. Illustratively, a second bipolar input conductor may be fixed within second forceps arm housing 215 wherein the second bipolar input conductor is electrically connected to second forceps arm 100.

In one or more embodiments, electrosurgical generator adaptor 240 may comprise a first electrosurgical generator interface 245 and a second electrosurgical generator interface 245. Illustratively, first electrosurgical generator interface 245 and second electrosurgical generator interface 245 may be configured to connect to an electrosurgical generator. In one or more embodiments, connecting first electrosurgical generator interface 245 and second electrosurgical generator interface 245 to an electrosurgical generator may be configured to electrically connect a first bipolar input conductor to a first electrosurgical generator output and to electrically connect a second bipolar input conductor to a second electrosurgical generator output. Illustratively, connecting a first bipolar input conductor to a first electrosurgical generator output may be configured to electrically connect first forceps arm 100 to the first electrosurgical generator output. In one or more embodiments, connecting a second bipolar input conductor to a second electrosurgical generator output may be configured to electrically connect second forceps arm 100 to the second electrosurgical generator output.

Illustratively, forceps arms 100 may be fixed within forceps arm housings 215 wherein forceps arm proximal ends 102 are fixed within input conductor isolation mechanism 210 and forceps arm distal ends 101 are separated by a maximum conductor tip 110 separation distance. In one or more embodiments, a surgeon may decrease a distance between first forceps arm distal end 101 and second forceps arm distal end 101, e.g., by applying a force to a lateral portion of forceps arms 100. Illustratively, a surgeon may decrease a distance between first forceps arm distal end 101 and second forceps arm distal end 101, e.g., until first forceps arm distal end 101 contacts second forceps arm distal end 101. In one or more embodiments, a contact between first forceps arm distal end 101 and second forceps arm distal end 101 may be configured to electrically connect conductor tips 110. Illustratively, an electrical connection of conductor tips 110 may be configured to close an electrical circuit. In one or more embodiments, a surgeon may increase a distance between first forceps arm distal end 101 and second forceps arm distal end 101, e.g., by reducing a force applied to a lateral portion of forceps arms 100. Illustratively, increasing a distance between first forceps arm distal end 101 and second forceps arm distal end 101 may be configured to separate conductor tips 110. In one or more embodiments, a separation of conductor tips 110 may be configured to open an electrical circuit.

Figure 3B:
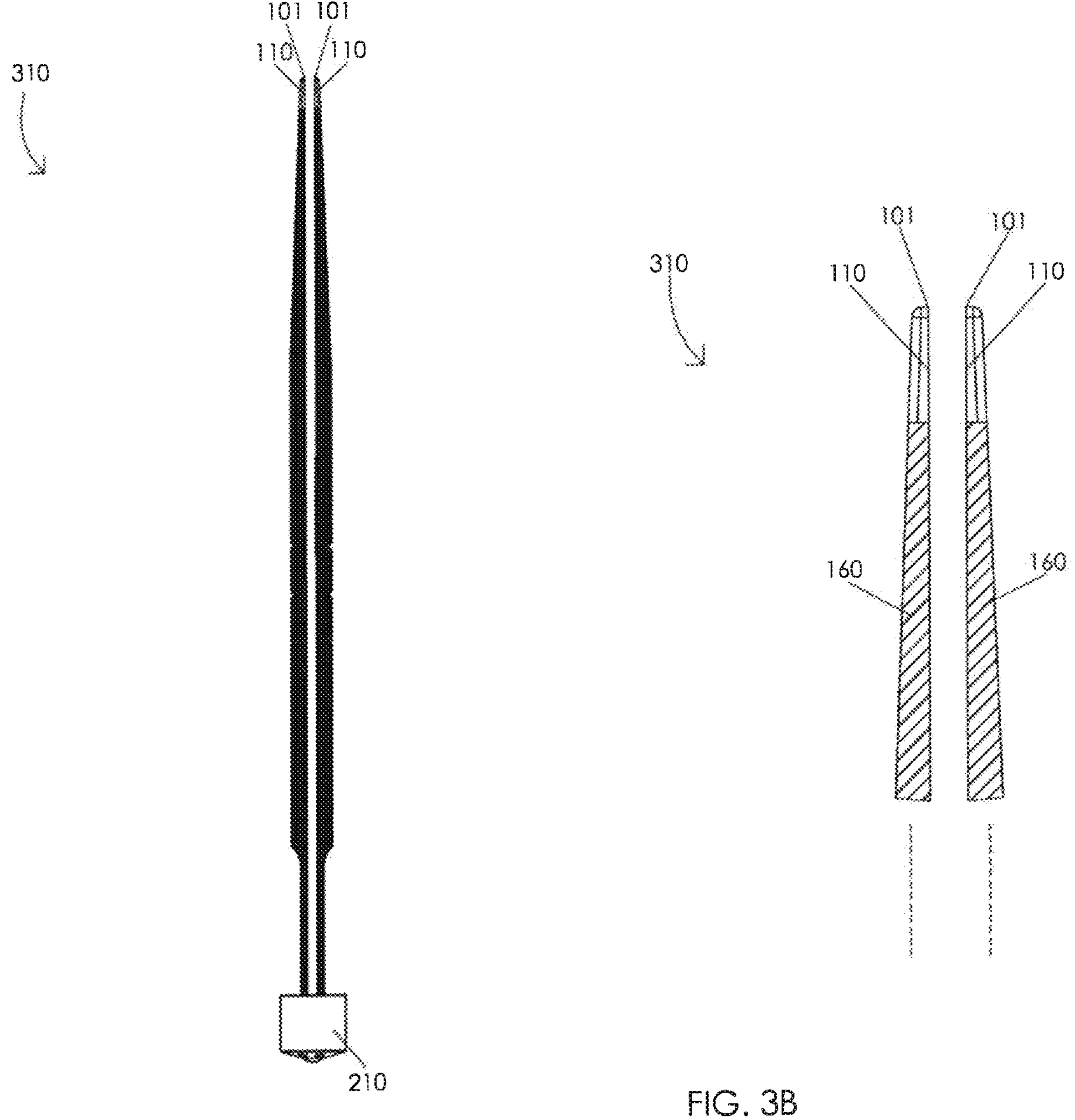

FIGS. 3A, 3B, 3C, 3D, and 3E are schematic diagrams illustrating a gradual closing of a bipolar forceps. FIG. 3A illustrates forceps jaws in an open orientation 300. Illustratively, forceps jaws 160 may comprise forceps jaws in an open orientation 300, e.g., when forceps arm distal ends 101 are separated by a maximum conductor tip 110 separation distance. In one or more embodiments, forceps arm distal ends 101 may be separated by a distance in a range of 0.5 to 0.7 inches when forceps jaws 160 comprise forceps jaws in an open orientation 300, e.g., forceps arm distal ends 101 may be separated by a distance of 0.625 inches when forceps jaws 160 comprise forceps jaws in an open orientation 300. Illustratively, forceps arm distal ends 101 may be separated by a distance less than 0.5 inches or greater than 0.7 inches when forceps jaws 160 comprise forceps jaws in an open orientation 300. In one or more embodiments, forceps jaws 160 may comprise forceps jaws in an open orientation 300, e.g., when no force is applied to a lateral portion of forceps arms 100.

FIG. 3B illustrates forceps jaws in a partially closed orientation 310. Illustratively, an application of a force to a lateral portion of forceps arms 100 may be configured to gradually close forceps jaws 160 from forceps jaws in an open orientation 300 to forceps jaws in a partially closed orientation 310. In one or more embodiments, an application of a force to a lateral portion of forceps arms 100 may be configured to decrease a distance between first forceps arm distal end 101 and second forceps arm distal end 101. Illustratively, an application of a force having a magnitude in a range of 0.05 to 0.3 pounds to a lateral portion of forceps arms 100 may be configured to decrease a distance between first forceps arm distal end 101 and second forceps arm distal end 101, e.g., an application of a force having a magnitude of 0.2 pounds to a lateral portion of forceps arms 100 may be configured to decrease a distance between first forceps arm distal end 101 and second forceps arm distal end 101. In one or more embodiments, an application of a force having a magnitude less than 0.05 pounds or greater than 0.3 pounds to a lateral portion of forceps arms 100 may be configured to decrease a distance between first forceps arm distal end 101 and second forceps arm distal end 101. Illustratively, a decrease of a distance between first forceps arm distal end 101 and second forceps arm distal end 101 may be configured to decrease a distance between conductor tips 110. In one or more embodiments, an application of a force having a magnitude in a range of 0.05 to 0.3 pounds to a lateral portion of forceps arms 100 may be configured to gradually close forceps jaws 160 from forceps jaws in an open orientation 300 to forceps jaws in a partially closed orientation 310. Illustratively, an application of a force having a magnitude less than 0.05 pounds or greater than 0.3 pounds to a lateral portion of forceps arms 100 may be configured to gradually close forceps jaws 160 from forceps jaws in an open orientation 300 to forceps jaws in a partially closed orientation 310. In one or more embodiments, an amount of force applied to a lateral portion of forceps arms 100 configured to close forceps jaws 160 to forceps jaws in a partially closed orientation 310 and a total mass of a bipolar forceps may have a force applied to total mass ratio in a range of 1.36 to 8.19, e.g., an amount of force applied to a lateral portion of forceps arms 100 configured to close forceps jaws 160 to forceps jaws in a partially closed orientation 310 and a total mass of a bipolar forceps may have a force applied to total mass ratio of 5.46. Illustratively, an amount of force applied to a lateral portion of forceps arms 100 configured to close forceps jaws 160 to forceps jaws in a partially closed orientation 310 and a total mass of a bipolar forceps may have a force applied to total mass ratio less than 1.36 or greater than 8.19.

In one or more embodiments, a surgeon may dispose a tissue between a first forceps arm conductor tip 110 and a second forceps arm conductor tip 110, e.g., a surgeon may dispose a tumor tissue between a first forceps arm conductor tip 110 and a second forceps arm conductor tip 110. Illustratively, disposing a tissue between a first forceps arm conductor tip 110 and a second forceps arm conductor tip 110 may be configured to electrically connect the first forceps arm conductor tip 110 and the second forceps arm conductor tip 110, e.g., the tissue may electrically connect the first forceps arm conductor tip 110 and the second forceps arm conductor tip 110. In one or more embodiments, electrically connecting a first forceps arm conductor tip 110 and a second forceps arm conductor tip 110 may be configured to apply an electrical current to a tissue. Illustratively, applying an electrical current to a tissue may be configured to coagulate the tissue, cauterize the tissue, ablate the tissue, etc. In one or more embodiments, electrically connecting a first forceps arm conductor tip 110 and a second forceps arm conductor tip 110 may be configured to seal a vessel, induce hemostasis, etc.

Figure 3C:
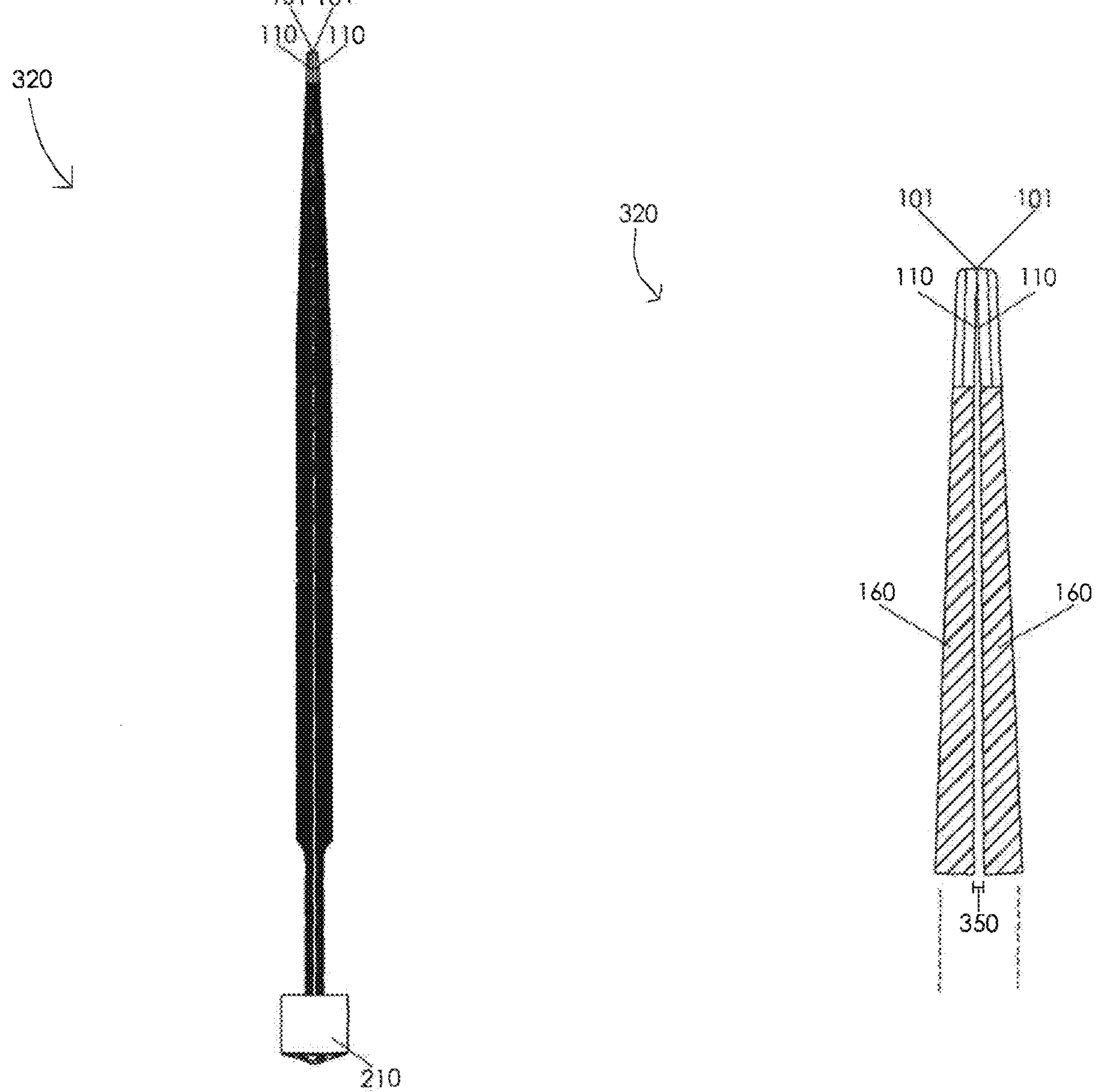

FIG. 3C illustrates forceps jaws in a first closed orientation 320. Illustratively, an application of a force to a lateral portion of forceps arms 100 may be configured to gradually close forceps jaws 160 from forceps jaws in a partially closed orientation 310 to forceps jaws in a first closed orientation 320. In one or more embodiments, an application of a force to a lateral portion of forceps arms 100 may be configured to decrease a distance between first forceps arm distal end 101 and second forceps arm distal end 101. Illustratively, a decrease of a distance between first forceps arm distal end 101 and second forceps arm distal end 101 may be configured to cause first forceps arm distal end 101 to contact second forceps arm distal end 101. In one or more embodiments, an application of a force having a magnitude in a range of 0.35 to 0.7 pounds to a lateral portion of forceps arms 100 may be configured to cause first forceps arm distal end 101 to contact second forceps arm distal end 101, e.g., an application of a force having a magnitude of 0.5 pounds to a lateral portion of forceps arms 100 may be configured to cause first forceps arm distal end 101 to contact second forceps arm distal end 101. Illustratively, an application of a force having a magnitude less than 0.35 pounds or greater than 0.7 pounds to a lateral portion of forceps arms 100 may be configured to cause first forceps arm distal end 101 to contact second forceps arm distal end 101. In one or more embodiment, an application of a force having a magnitude in a range of 0.35 to 0.7 pounds to a lateral portion of forceps arms 100 may be configured to gradually close forceps jaws 160 from forceps jaws in a partially closed orientation 310 to forceps jaws in a first closed orientation 320. Illustratively, an application of a force having a magnitude less than 0.35 pounds or greater than 0.7 pounds to a lateral portion of forceps arms 100 may be configured to gradually close forceps jaws 160 from forceps jaws in a partially closed orientation 310 to forceps jaws in a first closed orientation 320. In one or more embodiments, an amount of force applied to a lateral portion of forceps arms 100 configured to close forceps jaws 160 to forceps jaws in a first closed orientation 320 and a total mass of a bipolar forceps may have a force applied to total mass ratio in a range of 9.56 to 19.11, e.g., an amount of force applied to a lateral portion of forceps arms 100 configured to close forceps jaws 160 to forceps jaws in a first closed orientation 320 and a total mass of a bipolar forceps may have a force applied to total mass ratio of 13.65. Illustratively, an amount of force applied to a lateral portion of forceps arms 100 configured to close forceps jaws 160 to forceps jaws in a first closed orientation 320 and a total mass of a bipolar forceps may have a force applied to total mass ratio less than 9.56 or greater than 19.11.

In one or more embodiments, forceps jaws 160 may comprise forceps jaws in a first closed orientation 320, e.g., when first forceps arm distal end 101 contacts second forceps arm distal end 101 and no other portion of first forceps arm 100 contacts second forceps arm 100. Illustratively, forceps jaws 160 may comprise forceps jaws in a first closed orientation 320, e.g., when a distal end of a first forceps arm conductor tip 110 contacts a distal end of a second forceps arm conductor tip 110 and no other portion of first forceps arm 100 contacts second forceps arm 100. In one or more embodiments, first forceps arm conductor tip 110 and second forceps arm conductor tip 110 may have a contact area in a range of 0.0005 to 0.002 square inches when forceps jaws 160 comprise forceps jaws in a first closed orientation 320, e.g., first forceps arm conductor tip 110 and second forceps arm conductor tip 110 may have a contact area of 0.0016 square inches when forceps jaws 160 comprise forceps jaws in a first closed orientation 320. Illustratively, first forceps arm conductor tip 110 and second forceps arm conductor tip 110 may have a contact area of less than 0.0005 square inches or greater than 0.002 square inches when forceps jaws 160 comprise forceps jaws in a first closed orientation 320. In one or more embodiments, a proximal end of a first forceps arm conductor tip 110 may be separated from a proximal end of a second forceps arm conductor tip 110, e.g., when forceps jaws 160 comprise forceps jaws in a first closed orientation 320. Illustratively, a proximal end of a first forceps arm conductor tip 110 may be separated from a proximal end of a second forceps arm conductor tip 110 by a distance in a range of 0.005 to 0.015 inches when forceps jaws 160 comprise forceps jaws in a first closed orientation 320, e.g., a proximal end of a first forceps arm conductor tip 110 may be separated from a proximal end of a second forceps arm conductor tip 110 by a distance of 0.01 inches when forceps jaws 160 comprise forceps jaws in a first closed orientation 320. In one or more embodiments, a proximal end of a first forceps arm conductor tip 110 may be separated from a proximal end of a second forceps arm conductor tip 110 by a distance less than 0.005 inches or greater than 0.015 inches when forceps jaws 160 comprise forceps jaws in a first closed orientation 320.

Illustratively, forceps jaws 160 may comprise forceps jaws in a first closed orientation 320, e.g., when a distal end of a first forceps jaw 160 contacts a distal end of a second forceps jaw 160 and no other portion of first forceps arm 100 contacts second forceps arm 100. In one or more embodiments, a proximal end of a first forceps jaw 160 may be separated from a proximal end of a second forceps jaw 160 by a first separation distance 350, e.g., when forceps jaws 160 comprise forceps jaws in a first closed orientation 320. Illustratively, a proximal end of a first forceps jaw 160 may be separated from a proximal end of a second forceps jaw 160 by a first separation distance 350 in a range of 0.05 to 0.15 inches when forceps jaws 160 comprise forceps jaws in a first closed orientation 320, e.g., a proximal end of a first forceps jaw 160 may be separated from a proximal end of a second forceps jaw 160 by a first separation distance 350 of 0.1 inches when forceps jaws 160 comprise forceps jaws in a first closed orientation 320. In one or more embodiments, a proximal end of a first forceps jaw 160 may be separated from a proximal end of a second forceps jaw 160 by a first separation distance 350 less than 0.05 inches or greater than 0.15 inches when forceps jaws 160 comprise forceps jaws in a first closed orientation 320.

Illustratively, forceps jaws 160 may comprise forceps jaws in a first closed orientation 320, e.g., when a distal end of a first forceps arm conductor tip 110 contacts a distal end of a second forceps arm conductor tip 110. In one or more embodiments, a contact between a distal end of a first forceps arm conductor tip 110 and a distal end of a second forceps arm conductor tip 110 may be configured to electrically connect the first forceps arm conductor tip 110 and the second forceps arm conductor tip 110. Illustratively, forceps jaws 160 may comprise forceps jaws in a first closed orientation 320, e.g., when a first forceps arm conductor tip 110 is electrically connected to a second forceps arm conductor tip 110. In one or more embodiments, an electrical connection of a first forceps arm conductor tip 110 and a second forceps arm conductor tip 110 may be configured to cause an electrical current to flow from the first forceps arm conductor tip 110 into the second forceps arm conductor tip 110. Illustratively, an electrical connection of a first forceps arm conductor tip 110 and a second forceps arm conductor tip 110 may be configured to cause an electrical current to flow from the second forceps arm conductor tip 110 into the first forceps arm conductor tip 110. In one or more embodiments, electrically connecting a first forceps arm conductor tip 110 and a second forceps arm conductor tip 110 may be configured to increase a temperature of forceps arm distal ends 101, e.g., a surgeon may contact a tissue with forceps arm distal ends 101 to cauterize the tissue, coagulate the tissue, etc.

Figure 3D:
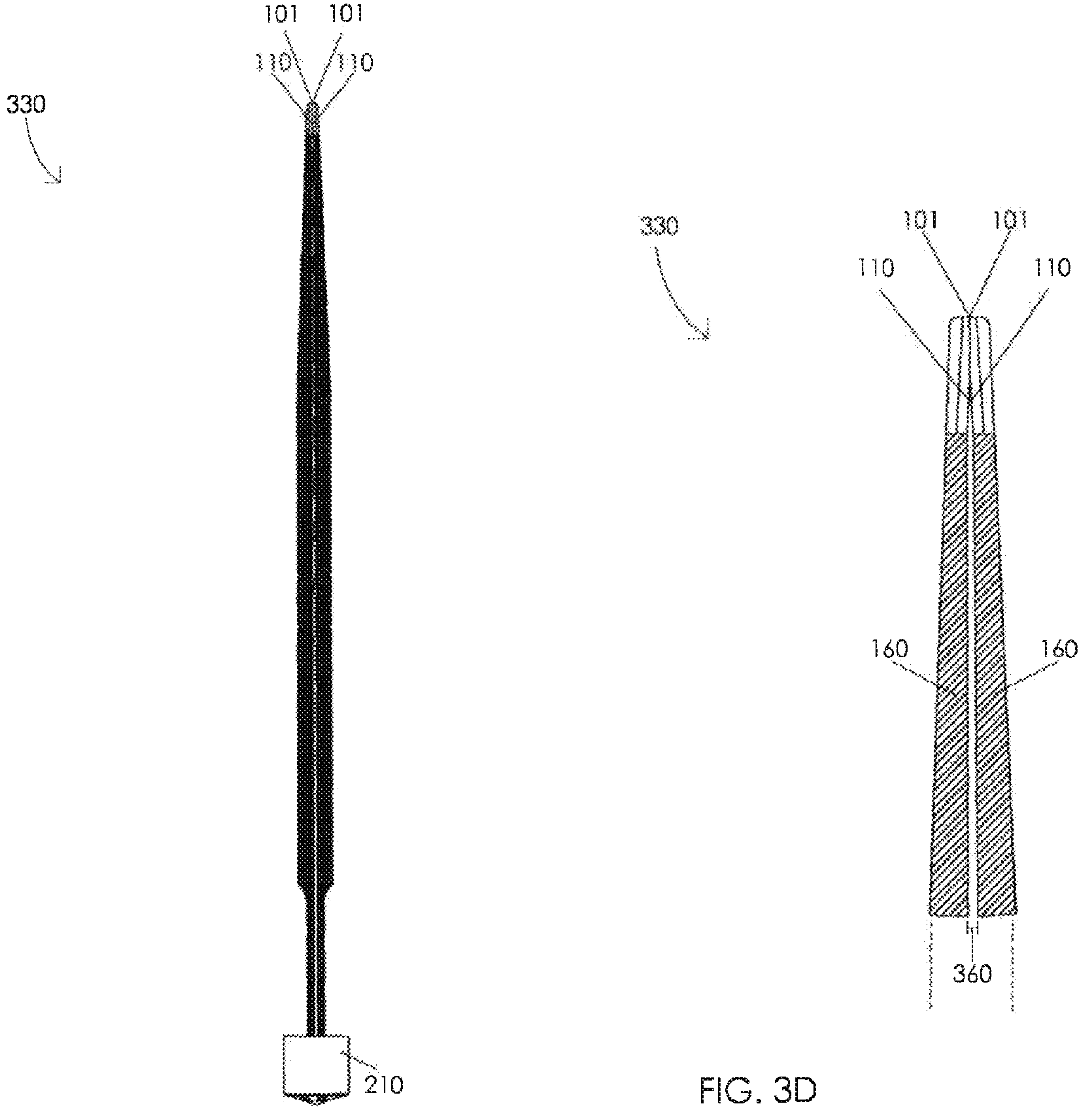

FIG. 3D illustrates forceps jaws in a second closed orientation 330. Illustratively, an application of a force to a lateral portion of forceps arms 100 may be configured to gradually close forceps jaws 160 from forceps jaws in a first closed orientation 320 to forceps jaws in a second closed orientation 330. In one or more embodiments, an application of a force to a lateral portion of forceps arms 100 may be configured to decrease a distance between a proximal end of first forceps arm conductor tip 110 and a proximal end of second forceps arm conductor tip 110. Illustratively, an application of a force to a lateral portion of forceps arms 100 may be configured to flex forceps jaws in a first closed orientation 320, e.g., an application of a force to a lateral portion of forceps arms 100 may be configured to gradually increase a contact area between first forceps arm conductor tip 110 and second forceps arm conductor tip 110. In one or more embodiments, an application of a force having a magnitude in a range of 0.8 to 1.4 pounds to a lateral portion of forceps arms 100 may be configured to gradually increase a contact area between first forceps arm conductor tip 110 and second forceps arm conductor tip 110, e.g., an application of a force having a magnitude of 1.1 pounds to a lateral portion of forceps arms 100 may be configured to gradually increase a contact area between first forceps arm conductor tip 110 and second forceps arm conductor tip 110. Illustratively, an application of a force having a magnitude less than 0.8 pounds or greater than 1.4 pounds to a lateral portion of forceps arms 100 may be configured to gradually increase a contact area between first forceps arm conductor tip 110 and second forceps arm conductor tip 110. In one or more embodiments, an application of a force having a magnitude in a range of 0.8 to 1.4 pounds to a lateral portion of forceps arms 100 may be configured to gradually close forceps jaws 160 from forceps jaws in a first closed orientation 320 to forceps jaws in a second closed orientation 330. Illustratively, an application of a force having a magnitude less than 0.8 pounds or greater than 1.4 pounds to a lateral portion of forceps arms 100 may be configured to gradually close forceps jaws 160 from forceps jaws in a first closed orientation 320 to forceps jaws in a second closed orientation 330. In one or more embodiments, an amount of force applied to a lateral portion of forceps arms 100 configured to close forceps jaws 160 to forceps jaws in a second closed orientation 330 and a total mass of a bipolar forceps may have a force applied to total mass ratio in a range of 21.84 to 38.22, e.g., an amount of force applied to a lateral portion of forceps arms 100 configured to close forceps jaws 160 to forceps jaws in a second closed orientation 330 and a total mass of a bipolar forceps may have a force applied to total mass ratio of 30.03. Illustratively, an amount of force applied to a lateral portion of forceps arms 100 configured to close forceps jaws 160 to forceps jaws in a second closed orientation 330 and a total mass of a bipolar forceps may have a force applied to total mass ratio less than 21.84 or greater than 38.22.

In one or more embodiments, first forceps arm conductor tip 110 and second forceps arm conductor tip 110 may have a contact area in a range of 0.001 to square inches when forceps jaws 160 comprise forceps jaws in a second closed orientation 330, e.g., first forceps arm conductor tip 110 and second forceps arm conductor tip 110 may have a contact area of 0.0025 square inches when forceps jaws 160 comprise forceps jaws in a second closed orientation 330. Illustratively, first forceps arm conductor tip 110 and second forceps arm conductor tip 110 may have a contact area less than 0.001 square inches or greater than 0.005 square inches when forceps jaws 160 comprise forceps jaws in a second closed orientation 330. In one or more embodiments, a proximal end of a first forceps arm conductor tip 110 may be separated from a proximal end of a second forceps arm conductor tip 110, e.g., when forceps jaws 160 comprise forceps jaws in a second closed orientation 330. Illustratively, a proximal end of a first forceps arm conductor tip 110 may be separated from a proximal end of a second forceps arm conductor tip 110 by a distance in a range of 0.001 to 0.0049 inches when forceps jaws 160 comprise forceps jaws in a second closed orientation 330, e.g., a proximal end of a first forceps arm conductor tip 110 may be separated from a proximal end of a second forceps arm conductor tip 110 by a distance of 0.0025 inches when forceps jaws 160 comprise forceps jaws in a second closed orientation 330. In one or more embodiments, a proximal end of a first forceps arm conductor tip 110 may be separated from a proximal end of a second forceps arm conductor tip 110 by a distance less than 0.001 inches or greater than 0.0049 inches when forceps jaws 160 comprise forceps jaws in a second closed orientation 330.

Illustratively, forceps jaws 160 may comprise forceps jaws in a second closed orientation 330, e.g., when a distal end of a first forceps jaw 160 contacts a distal end of a second forceps jaw 160. In one or more embodiments, a proximal end of a first forceps jaw 160 may be separated from a proximal end of a second forceps jaw 160 by a second separation distance 360, e.g., when forceps jaws 160 comprise forceps jaws in a second closed orientation 330. Illustratively, a proximal end of a first forceps jaw 160 may be separated from a proximal end of a second forceps jaw 160 by a second separation distance 360 in a range of 0.01 to 0.049 inches when forceps jaws 160 comprise forceps jaws in a second closed orientation 330, e.g., a proximal end of a first forceps jaw 160 may be separated from a proximal end of a second forceps jaw 160 by a second separation distance 360 of 0.03 inches when forceps jaws 160 comprise forceps jaws in a second closed orientation 330. In one or more embodiments, a proximal end of a first forceps jaw 160 may be separated from a proximal end of a second forceps jaw 160 by a second separation distance 360 less than 0.01 inches or greater than 0.049 inches when forceps jaws 160 comprise forceps jaws in a second closed orientation 330.

Illustratively, forceps jaws 160 may comprise forceps jaws in a second closed orientation 330, e.g., when a first forceps arm conductor tip 110 contacts a second forceps arm conductor tip 110. In one or more embodiments, a contact between a first forceps arm conductor tip 110 and a second forceps arm conductor tip 110 may be configured to electrically connect the first forceps arm conductor tip 110 and the second forceps arm conductor tip 110. Illustratively, forceps jaws 160 may comprise forceps jaws in a second closed orientation 330, e.g., when a first forceps arm conductor tip 110 is electrically connected to a second forceps arm conductor tip 110. In one or more embodiments, an electrical connection of a first forceps arm conductor tip 110 and a second forceps arm conductor tip 110 may be configured to cause an electrical current to flow from the first forceps arm conductor tip 110 into the second forceps arm conductor tip 110. Illustratively, an electrical connection of a first forceps arm conductor tip 110 and a second forceps arm conductor tip 110 may be configured to cause an electrical current to flow from the second forceps arm conductor tip 110 into the first forceps arm conductor tip 110. In one or more embodiments, electrically connecting a first forceps arm conductor tip 110 and a second forceps arm conductor tip 110 may be configured to increase a temperature of forceps arm conductor tips 110, e.g., a surgeon may contact a tissue with forceps arm conductor tips 110 to cauterize the tissue, coagulate the tissue, etc.

Figure 3E:
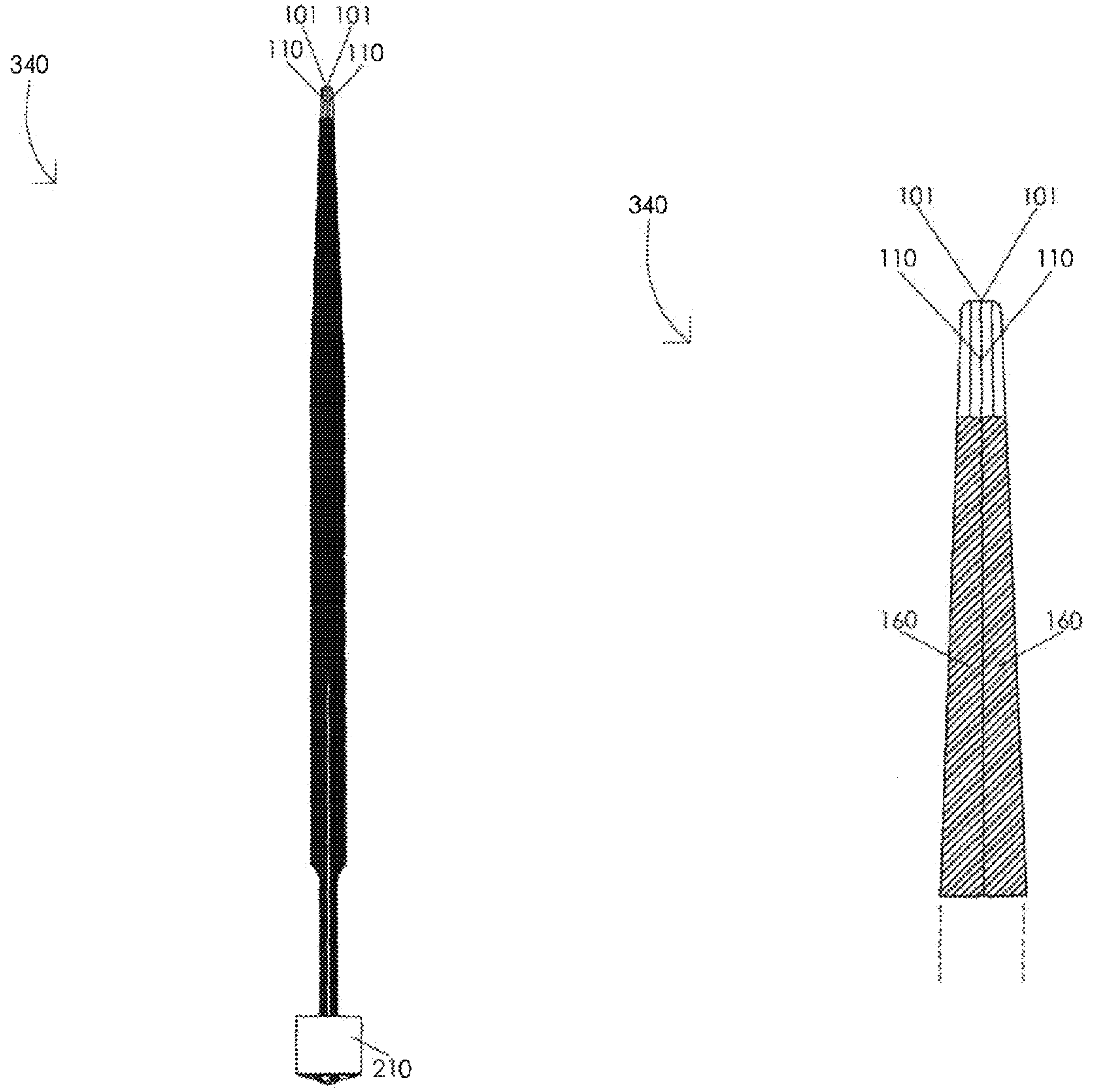

FIG. 3E illustrates forceps jaws in a fully closed orientation 340. Illustratively, an application of a force to a lateral portion of forceps arms 100 may be configured to gradually close forceps jaws 160 from forceps jaws in a second closed orientation 330 to forceps jaws in a fully closed orientation 340. In one or more embodiments, an application of a force to a lateral portion of forceps arms 100 may be configured to decrease a distance between a proximal end of first forceps arm conductor tip 110 and a proximal end of second forceps arm conductor tip 110. Illustratively, an application of a force to a lateral portion of forceps arms 100 may be configured to gradually increase a contact area between first forceps arm conductor tip 110 and second forceps arm conductor tip 110 until a proximal end of first forceps arm conductor tip 110 contacts a proximal end of second forceps arm conductor tip 110. In one or more embodiments, a proximal end of first forceps arm conductor tip 110 may contact a proximal end of second forceps arm conductor tip 110, e.g., when forceps jaws 160 comprise forceps jaws in a fully closed orientation 340. Illustratively, first forceps arm conductor tip 110 and second forceps arm conductor tip 110 may have a maximum contact area, e.g., when forceps jaws 160 comprise forceps jaws in a fully closed orientation 340. In one or more embodiments, first forceps arm conductor tip 110 and second forceps arm conductor tip 110 may have a contact area in a range of 0.01 to 0.015 square inches when forceps jaws 160 comprise forceps jaws in a fully closed orientation 340, e.g., first forceps arm conductor tip 110 and second forceps arm conductor tip 110 may have a contact area of 0.0125 square inches when forceps jaws 160 comprise forceps jaws in a fully closed orientation 340. Illustratively, first forceps arm conductor tip 110 and second forceps arm conductor tip 110 may have a contact area less than 0.01 square inches or greater than 0.015 square inches when forceps jaws 160 comprise forceps jaws in a fully closed orientation 340.

In one or more embodiments, an application of a force to a lateral portion of forceps arms 100 may be configured to gradually increase a contact area between first forceps jaw 160 and second forceps jaw 160. Illustratively, an application of a force to a lateral portion of forceps arms 100 may be configured to gradually increase a contract area between first forceps jaw 160 and second forceps jaw 160. In one or more embodiments, an application of a force to a lateral portion of forceps arms 100 may be configured to gradually increase a contact area between first forceps jaw 160 and second forceps jaw 160 until a proximal end of first forceps jaw 160 contacts a proximal end of second forceps jaw 160. Illustratively, a proximal end of first forceps jaw 160 may contact a proximal end of second forceps jaw 160, e.g., when forceps jaws 160 comprise forceps jaws in a fully closed orientation 340. In one or more embodiments, first forceps jaw 160 and second forceps jaw 160 may have a maximum contact area, e.g., when forceps jaws 160 comprise forceps jaws in a fully closed orientation 340. Illustratively, an application of a force having a magnitude in a range of 1.5 to 3.3 pounds to a lateral portion of forceps arms 100 may be configured to gradually close forceps jaws 160 from forceps jaws in a second closed orientation 330 to forceps jaws in a fully closed orientation 340, e.g., an application of a force having a magnitude of 2.5 pounds to a lateral portion of forceps arms may be configured to gradually close forceps jaws 160 from forceps jaws in a second closed orientation 330 to forceps jaws in a fully closed orientation 340. In one or more embodiments, an application of a force having a magnitude less than 1.5 pounds or greater than 3.3 pounds to a lateral portion of forceps arms 100 may be configured to gradually close forceps jaws 160 from forceps jaws in a second closed orientation 330 to forceps jaws in a fully closed orientation 340. Illustratively, an amount of force applied to a lateral portion of forceps arms 100 configured to close forceps jaws 160 to forceps jaws in a fully closed orientation 340 and a total mass of a bipolar forceps may have a force applied to total mass ratio in a range of 40.95 to 90.10, e.g., an amount of force applied to a lateral portion of forceps arms 100 configured to close forceps jaws 160 to forceps jaws in a fully closed orientation 340 and a total mass of a bipolar forceps may have a force applied to total mass ratio of 68.26. In one or more embodiments, an amount of force applied to a lateral portion of forceps arms 100 configured to close forceps jaws 160 to forceps jaws in a fully closed orientation 340 and a total mass of a bipolar forceps may have a force applied to total mass ratio less than 40.95 or greater than 90.10.

Figure 4A:
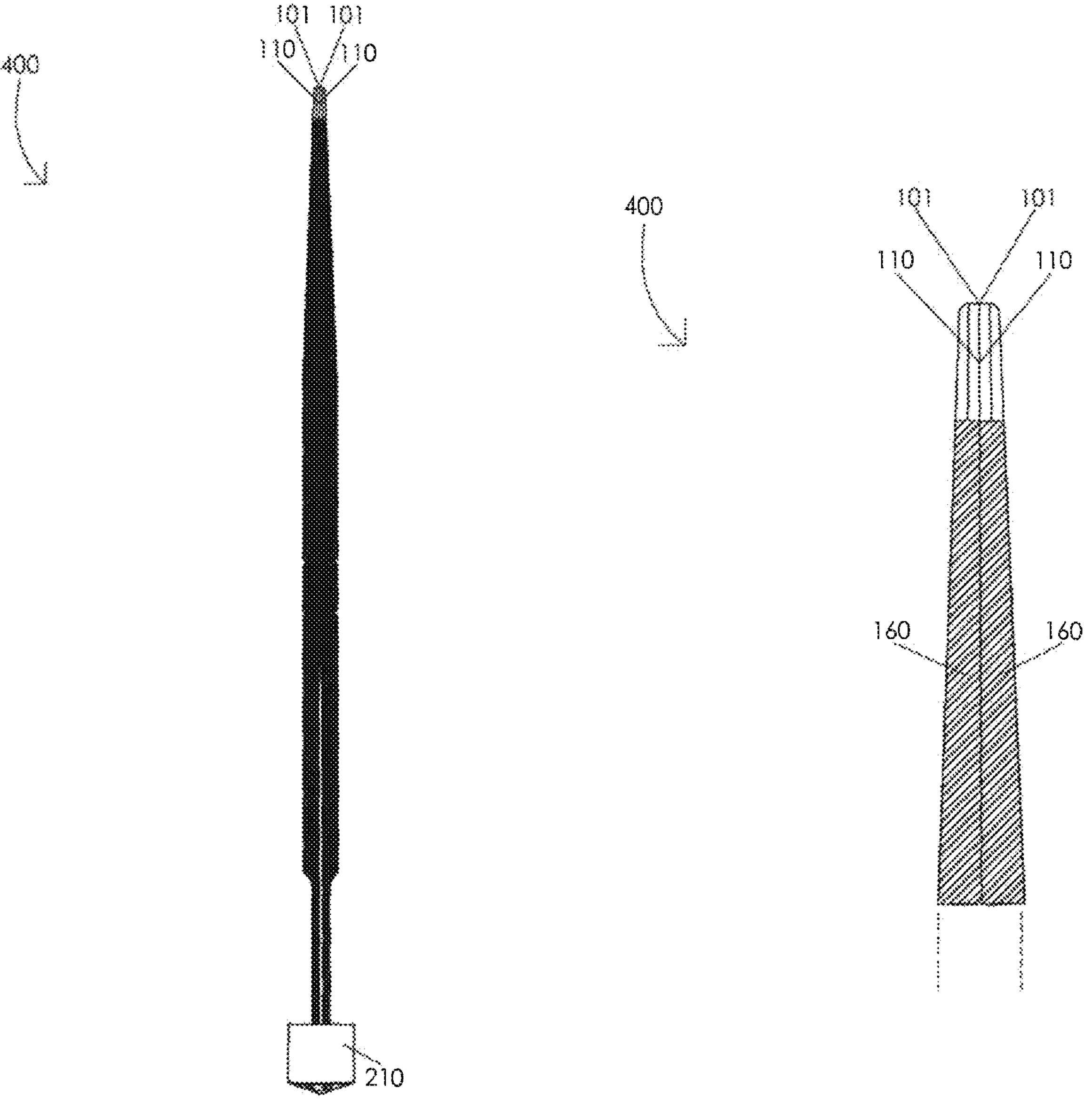

FIGS. 4A, 4B, 4C, 4D, and 4E are schematic diagrams illustrating a gradual opening of a bipolar forceps. FIG. 4A illustrates forceps jaws in a closed orientation 400. Illustratively, forceps jaws 160 may comprise forceps jaws in a closed orientation 400, e.g., when a first forceps arm conductor tip 110 contacts a second forceps arm conductor tip 110. In one or more embodiments, forceps jaws 160 may comprise forceps jaws in a closed orientation 400, e.g., when a distal end of a first forceps arm conductor tip 110 contacts a distal end of a second forceps arm conductor tip 110 and a proximal end of the first forceps arm conductor tip 110 contacts a proximal end of the second forceps arm conductor tip 110. Illustratively, forceps jaws 160 may comprise forceps jaws in a closed orientation 400, e.g., when a first forceps jaw 160 contacts a second forceps jaw 160. In one or more embodiments, forceps jaws 160 may comprise forceps jaws in a closed orientation 400, e.g., when a distal end of a first forceps jaw 160 contacts a distal end of a second forceps jaw 160 and a proximal end of the first forceps jaw 160 contacts a proximal end of the second forceps jaw 160. Illustratively, forceps jaws 160 may comprise forceps jaws in a closed orientation 400 when a force having a magnitude greater than 1.5 pounds is applied to a lateral portion of forceps arms 100, e.g., forceps jaws 160 may comprise forceps jaws in a closed orientation 400 when a force having a magnitude of 2.5 pounds is applied to a lateral portion of forceps arms 100. In one or more embodiments, forceps jaws 160 may comprise forceps jaws in a closed orientation 400 when a force less than or equal to 1.5 pounds is applied to a lateral portion of forceps arms 100.

Figure 4B:
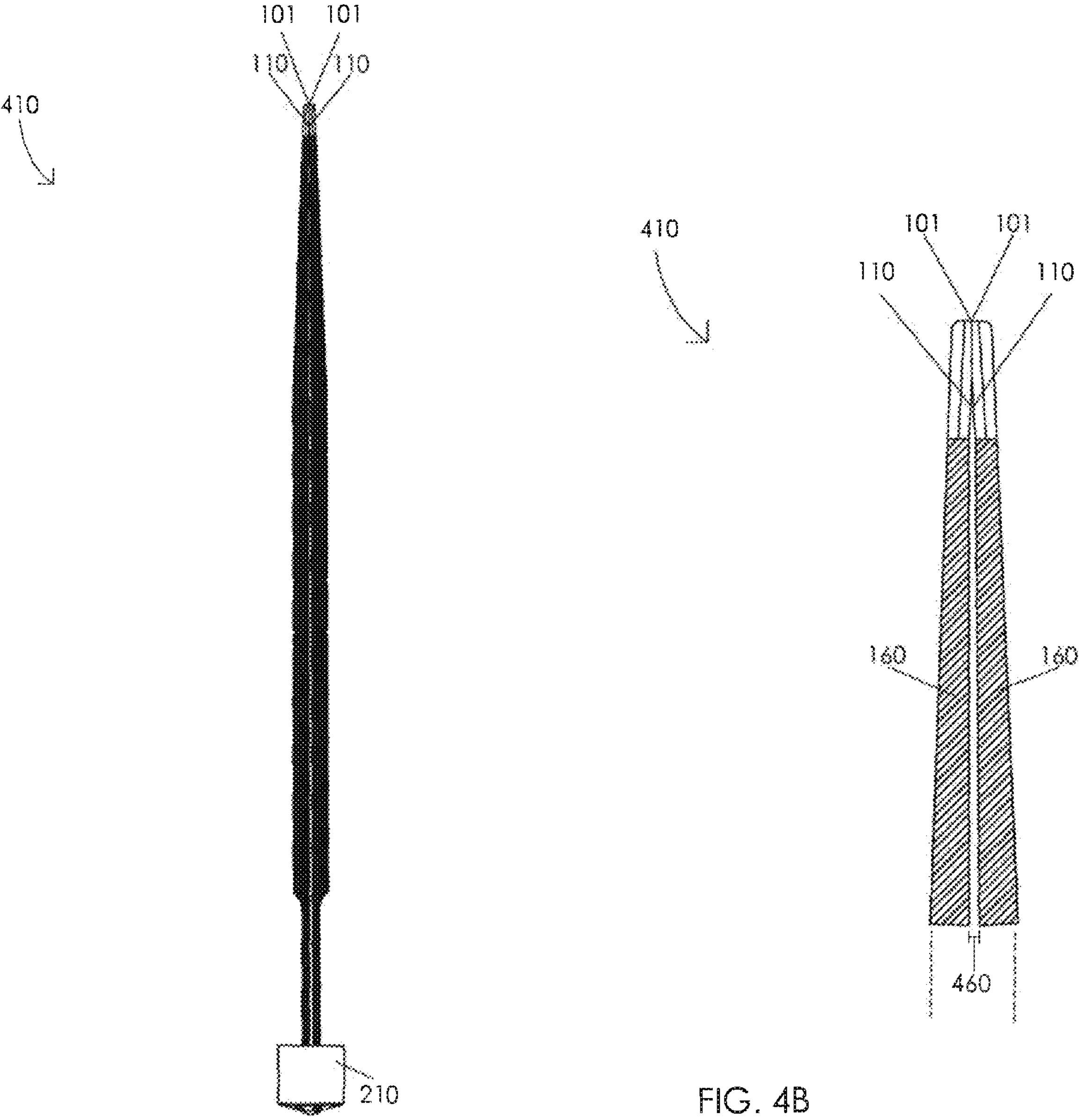

FIG. 4B illustrates forceps jaws in a first partially closed orientation 410. Illustratively, a reduction of a force applied to a lateral portion of forceps arms 100 may be configured to gradually open forceps jaws 160 from forceps jaws in a closed orientation 400 to forceps jaws in a first partially closed orientation 410. In one or more embodiments, a reduction of a force applied to a lateral portion of forceps arms 100 may be configured to separate proximal ends of forceps jaws 160. Illustratively, a reduction of a force applied to a lateral portion of forceps arms 100 may be configured to increase a distance between a proximal end of first forceps jaw 160 and a proximal end of second forceps jaw 160. In one or more embodiments, a proximal end of a first forceps jaw 160 may be separated from a proximal end of a second forceps jaw 160 by a first partially closed separation distance 460, e.g., when forceps jaws 160 comprise forceps jaws in a first partially closed orientation 410. Illustratively, a proximal end of a first forceps jaw 160 may be separated from a proximal end of a second forceps jaw 160 by a first partially closed separation distance 460 in a range of 0.01 to 0.049 inches when forceps jaws 160 comprise forceps jaws in a first partially closed orientation 410, e.g., a proximal end of a first forceps jaw 160 may be separated from a proximal end of a second forceps jaw 160 by a first partially closed separation distance 460 of 0.03 inches when forceps jaws 160 comprise forceps jaws in a first partially closed orientation 410. In one or more embodiments, a proximal end of a first forceps jaw 160 may be separated from a proximal end of a second forceps jaw 160 by a first partially closed separation distance 460 less than 0.01 inches or greater than 0.049 inches when forceps jaws 160 comprise forceps jaws in a first partially closed orientation 410. Illustratively, a reduction of a force applied to a lateral portion of forceps arms 100 may be configured to separate proximal ends of forceps arm conductor tips 110. In one or more embodiments, a reduction of a force applied to a lateral portion of forceps arms 100 may be configured to increase a separation distance between a proximal end of first forceps arm conductor tip 110 and a proximal end of second forceps arm conductor tip 110. Illustratively, a reduction of a force applied to a lateral portion of forceps arms 100 may be configured to reduce a contact area between first forceps arm conductor tip 110 and second forceps arm conductor tip 110. In one or more embodiments, a reduction of a force applied to a lateral portion of forceps arms 100 may be configured to spread a tissue, dissect a tissue, etc. Illustratively, a surgeon may insert forceps arm distal ends 101 into a tissue, e.g., when forceps jaws 160 comprise forceps jaws in a closed orientation 400. In one or more embodiments, the surgeon may reduce a force applied to a lateral portion of forceps arms 100 and gradually open forceps jaws 160 from forceps jaws in a closed orientation 400 to forceps jaws in a first partially closed orientation 410. Illustratively, gradually opening forceps jaws 160 from forceps jaws in a closed orientation 400 to forceps jaws in a first partially closed orientation 410 may be configured to spread the tissue, dissect the tissue, etc.

Figure 4C:
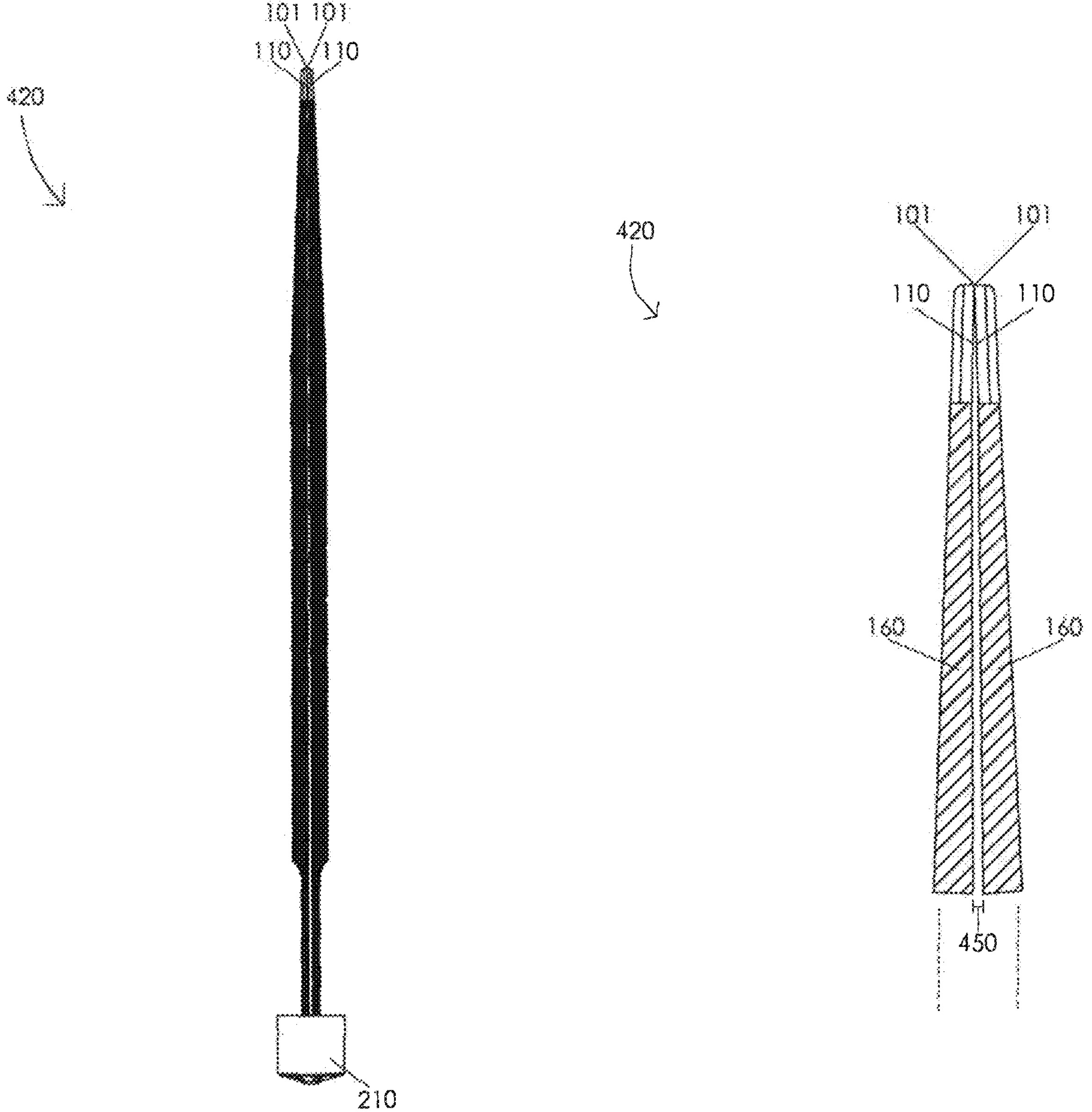

FIG. 4C illustrates forceps jaws in a second partially closed orientation 420.

Illustratively, a reduction of a force applied to a lateral portion of forceps arms 100 may be configured to gradually open forceps jaws 160 from forceps jaws in a first partially closed orientation 410 to forceps jaws in a second partially closed orientation 420. In one or more embodiments, a reduction of a force applied to a lateral portion of forceps arms 100 may be configured to separate proximal ends of forceps jaws 160. Illustratively, a reduction of a force applied to a lateral portion of forceps arms 100 may be configured to increase a distance between a proximal end of first forceps jaw 160 and a proximal end of second forceps jaw 160. In one or more embodiments, a proximal end of a first forceps jaw 160 may be separated from a proximal end of a second forceps jaw 160 by a second partially closed separation distance 450, e.g., when forceps jaws 160 comprise forceps jaws in a second partially closed orientation 420. Illustratively, a proximal end of a first forceps jaw 160 may be separated from a proximal end of a second forceps jaw 160 by a second partially closed separation distance 450 in a range of 0.05 to 0.15 inches when forceps jaws 160 comprise forceps jaws in a second partially closed orientation 420, e.g., a proximal end of a first forceps jaw 160 may be separated from a proximal end of a second forceps jaw 160 by a second partially closed separation distance 450 of 0.1 inches when forceps jaws 160 comprise forceps jaws in a second partially closed orientation 420. In one or more embodiments, a proximal end of a first forceps jaw 160 may be separated from a proximal end of a second forceps jaw 160 by a second partially closed separation distance 450 less than 0.05 inches or greater than 0.15 inches when forceps jaws 160 comprise forceps jaws in a second partially closed orientation 420. Illustratively, a reduction of a force applied to a lateral portion of forceps arms 100 may be configured to separate proximal ends of forceps arm conductor tips 110. In one or more embodiments, a reduction of a force applied to a lateral portion of forceps arms 100 may be configured to increase a separation distance between a proximal end of first forceps arm conductor tip 110 and a proximal end of second forceps arm conductor tip 110. Illustratively, a reduction of a force applied to a lateral portion of forceps arms 100 may be configured to reduce a contact area between first forceps arm conductor tip 110 and second forceps arm conductor tip 110. In one or more embodiments, a reduction of a force applied to a lateral portion of forceps arms 100 may be configured to spread a tissue, dissect a tissue, etc. Illustratively, a surgeon may insert forceps arm distal ends 101 into a tissue, e.g., when forceps jaws 160 comprise forceps jaws in a first partially closed orientation 410. In one or more embodiments, the surgeon may reduce a force applied to a lateral portion of forceps arms 100 and gradually open forceps jaws 160 from forceps jaws in a first partially closed orientation 410 to forceps jaws in a second partially closed orientation 420. Illustratively, gradually opening forceps jaws 160 from forceps jaws in a first partially closed orientation 410 to forceps jaws in a second partially closed orientation 420 may be configured to spread the tissue, dissect the tissue, etc.

Figure 4D:
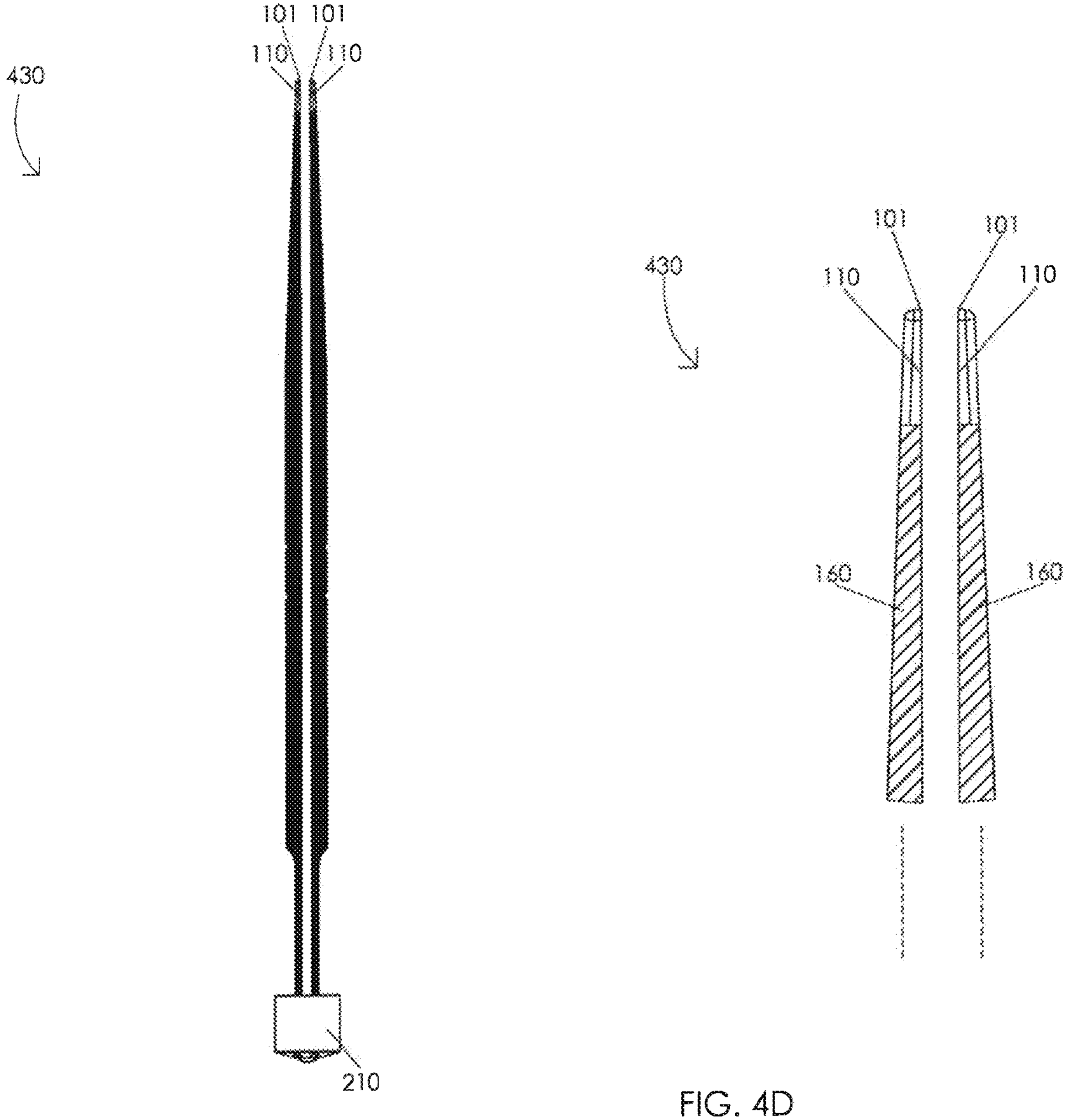

FIG. 4D illustrates forceps jaws in a partially open orientation 430. Illustratively, a reduction of a force applied to a lateral portion of forceps arms 100 may be configured to gradually open forceps jaws 160 from forceps jaws in a second partially closed orientation 420 to forceps jaws in a partially open orientation 430. In one or more embodiments, a distal end of first forceps jaw 160 may be separated from a distal end of second forceps jaw 160, e.g., when forceps jaws 160 comprise forceps jaws in a partially open orientation 430. Illustratively, a distal end of first forceps arm conductor tip 110 may be separated from a distal end of second forceps arm conductor tip 110, e.g., when forceps jaws 160 comprise forceps jaws in a partially open orientation 430. In one or more embodiments, a reduction of a force applied to a lateral portion of forceps arms 100 may be configured to electrically disconnect first forceps arm conductor tip 110 and second forceps arm conductor tip 110. Illustratively, first forceps arm conductor tip 110 may be electrically disconnected from second forceps arm conductor tip 110, e.g., when forceps jaws 160 comprise forceps jaws in a partially open orientation 430. In one or more embodiments, a reduction of a force applied to a lateral portion of forceps arms 100 may be configured to spread a tissue, dissect a tissue, etc. Illustratively, a surgeon may insert forceps arm distal ends 101 into a tissue, e.g., when forceps jaws 160 comprise forceps jaws in a second partially closed orientation 420. In one or more embodiments, the surgeon may reduce a force applied to a lateral portion of forceps arms 100 and gradually open forceps jaws 160 from forceps jaws in a second partially closed orientation 420 to forceps jaws in a partially open orientation 430. Illustratively, gradually opening forceps jaws 160 from forceps jaws in a second partially closed orientation 420 to forceps jaws in a partially open orientation 430 may be configured to spread the tissue, dissect the tissue, etc.

FIG. 4E illustrates forceps jaws in a fully open orientation 440. Illustratively, a reduction of a force applied to a lateral portion of forceps arms 100 may be configured to gradually open forceps jaws 160 from forceps jaws in a partially open orientation 430 to forceps jaws in a fully open orientation 440. In one or more embodiments, forceps arm distal ends 101 may be separated by a distance in a range of 0.5 to 0.7 inches when forceps jaws 160 comprise forceps jaws in a fully open orientation 440, e.g., forceps arm distal ends 101 may be separated by a distance of 0.625 inches when forceps jaws 160 comprise forceps jaws in a fully open orientation 440. Illustratively, forceps arm distal ends 101 may be separated by a distance less than 0.5 inches or greater than 0.7 inches when forceps jaws 160 comprise forceps jaws in a fully open orientation 440. In one or more embodiments, forceps jaws 160 may comprise forceps jaws in a fully open orientation 440, e.g., when no force is applied to a lateral portion of forceps arms 100.

Figure 5A:
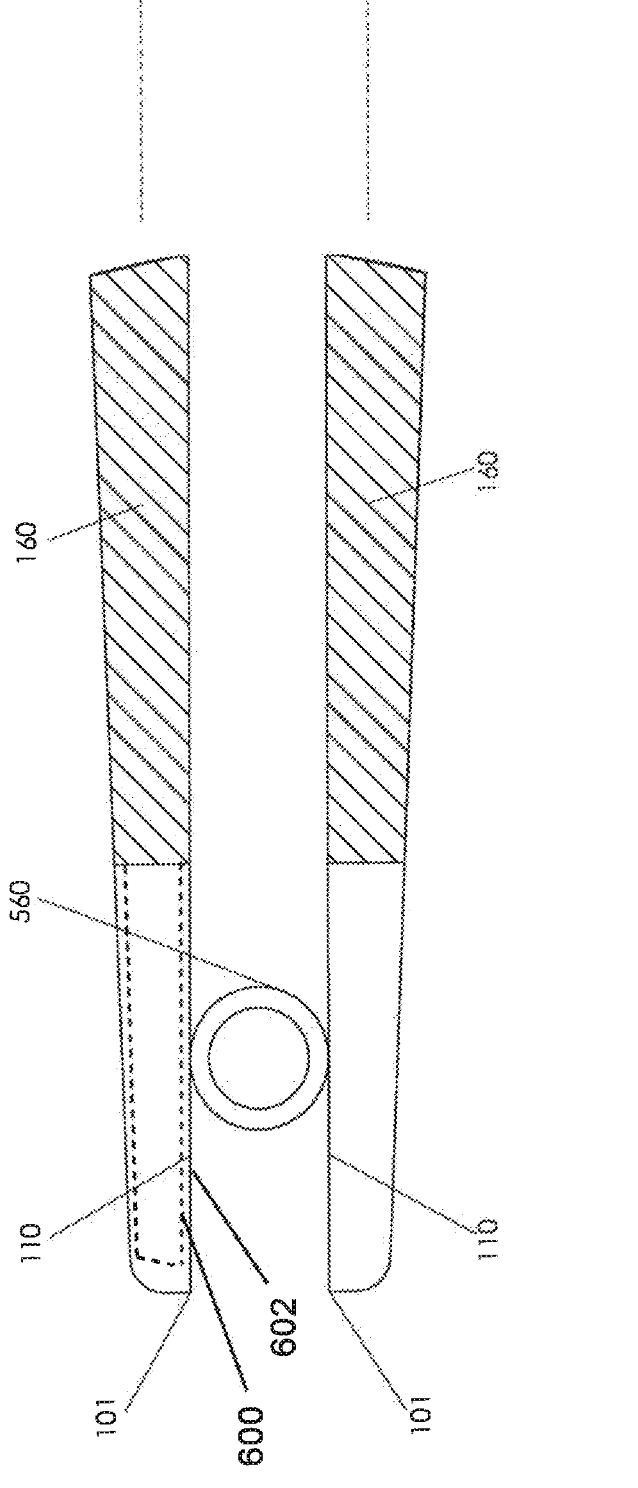
FIGS. 5A, 5B, and 5C are schematic diagrams illustrating a uniform compression of a vessel.
Figure 5B:
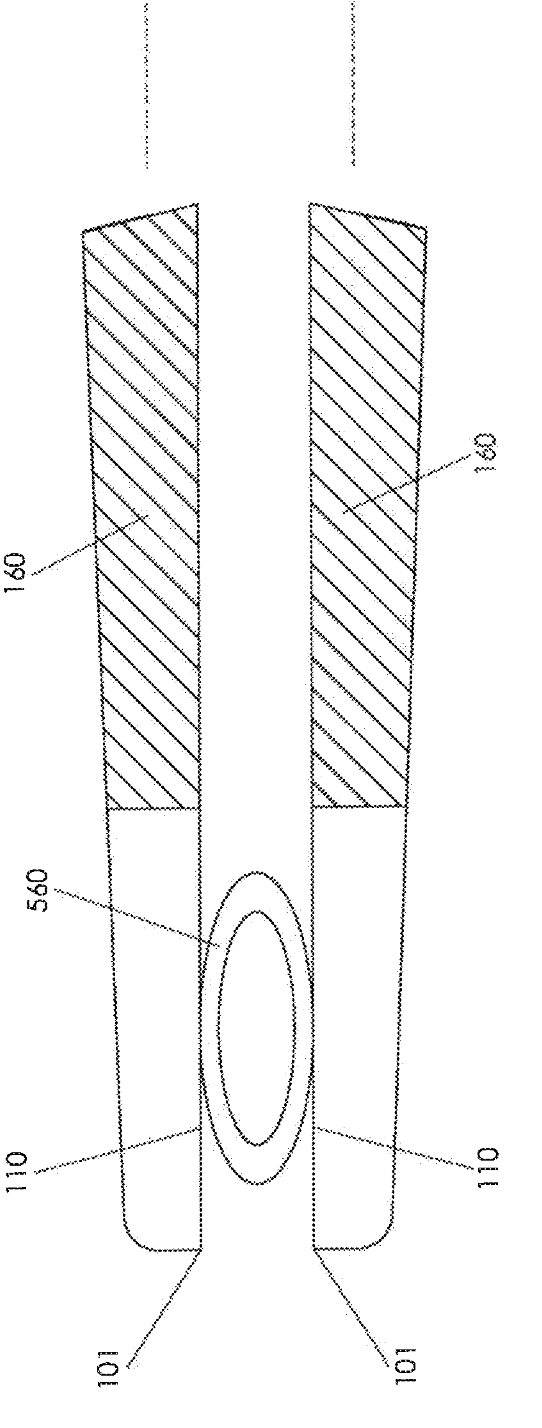
Figure 5C:
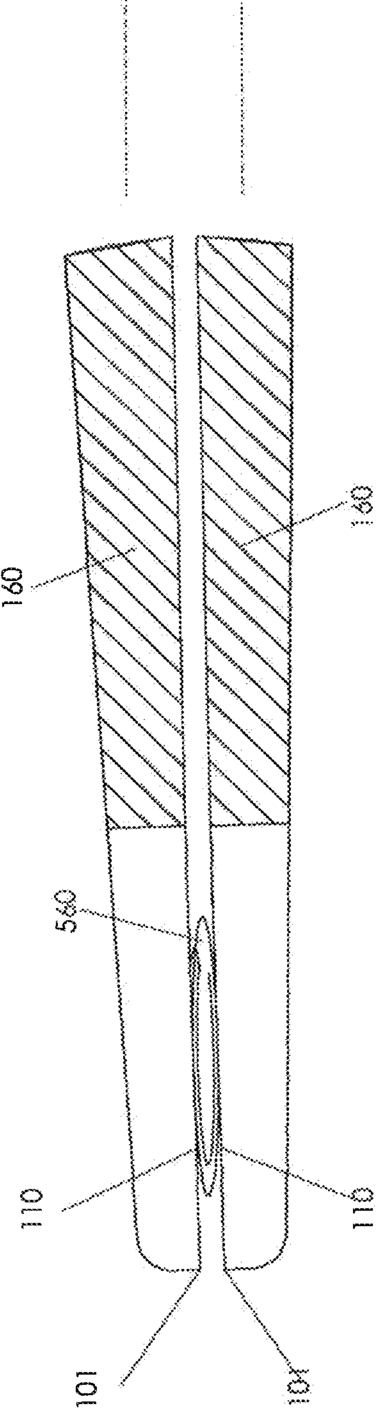

FIGS. 5A, 5B, and 5C are schematic diagrams illustrating a uniform compression of a vessel 560. In one or more embodiments, vessel 560 may comprise a blood vessel of an arteriovenous malformation. FIG. 5A illustrates an uncompressed vessel 500. Illustratively, vessel 560 may comprise an uncompressed vessel 500, e.g., when vessel 560 has a natural geometry. In one or more embodiments, vessel 560 may comprise an uncompressed vessel, e.g., when forceps jaws 160 comprise forceps jaws in a partially closed orientation 310. Illustratively, a surgeon may dispose vessel 560 between first forceps arm conductor tip 110 and second forceps arm conductor tip 110, e.g., when forceps jaws 160 comprise forceps jaws in an open orientation 300. In one or more embodiments, an application of a force to a lateral portion of forceps arms 100 may be configured to gradually close forceps jaws 160 from forceps jaws in an open orientation 300 to forceps jaws in a partially closed orientation 310. Illustratively, vessel 560 may electrically connect first forceps arm conductor tip 110 and second forceps arm conductor tip 110, e.g., when vessel 560 comprises an uncompressed vessel 500. In one or more embodiments, a surgeon may identify an orientation of forceps jaws 160 wherein conductor tips 110 initially contact vessel 560. Illustratively, a geometry of forceps arms 100 may be configured to allow a surgeon to visually identify an orientation of forceps jaws 160 wherein conductor tips 110 initially contact vessel 560. In one or more embodiments, a mass of forceps arms 100 may be configured to allow a surgeon to tactilely identify an orientation of forceps jaws 160 wherein conductor tips 110 initially contact vessel 560. Illustratively, a geometry of forceps arms 100 and a mass of forceps arms 100 may be configured to allow a surgeon to both visually and tactilely identify an orientation of forceps jaws 160 wherein conductor tips 110 initially contact vessel 560. Volumetric reduction of the size of the forceps arm 100 allows visibility of the surgical site. Volumetric reduction of the size of the forceps arm 100 allows improved thermal control of the conductor tips 110 by reducing the thermal mass of the material at the ends of the forceps arm 100 to keep the conductor tips 100 below a designated threshold temperature, which may correspond to damaging of patient tissue, making the conductor tips 110 less likely to damage targeted and non-targeted biological tissue, such as by sticking or charring, during operation.

FIG. 5B illustrates a partially compressed vessel 510. Illustratively, an application of a force to a lateral portion of forceps arms 100 may be configured to uniformly compress vessel 560 from an uncompressed vessel 500 to a partially compressed vessel 510. In one or more embodiments, an application of a force to a lateral portion of forceps arms 100 may be configured to uniformly increase a contact area between vessel 560 and forceps arm conductor tips 110. Illustratively, vessel 560 may electrically connect first forceps arm conductor tip 110 and second forceps arm conductor tip 110, e.g., when vessel 560 comprises a partially compressed vessel 510. In one or more embodiments, an application of a force to a lateral portion of forceps arms 100 may be configured to compress vessel 560 wherein vessel 560 maintains a symmetrical geometry with respect to a medial axis of vessel 560. Illustratively, vessel 560 may have a symmetrical geometry with respect to a medial axis of vessel 560 when vessel 560 comprises a partially compressed vessel 510. In one or more embodiments, forceps jaws 160 may be configured to compress vessel 560 wherein no portion of vessel 560 is compressed substantially more than another portion of vessel 560, e.g., forceps jaws 160 may be configured to evenly compress vessel 560 without pinching a first portion of vessel 560 or bulging a second portion of vessel 560. Illustratively, vessel 560 may be evenly compressed when vessel 560 comprises a partially compressed vessel 510.

FIG. 5C illustrates a fully compressed vessel 520. Illustratively, an application of a force to a lateral portion of forceps arms 100 may be configured to uniformly compress vessel 560 from a partially compressed vessel 510 to a fully compressed vessel 520. In one or more embodiments, an application of a force to a lateral portion of forceps arms 100 may be configured to uniformly increase a contact area between vessel 560 and forceps arm conductor tips 110. Illustratively, vessel 560 may electrically connect first forceps arm conductor tip 110 and second forceps arm conductor tip 110, e.g., when vessel 560 comprises a fully compressed vessel 520. In one or more embodiments, a surgeon may uniformly cauterize vessel 560, e.g., when vessel 560 comprises a fully compressed vessel 520. Illustratively, a surgeon may uniformly achieve hemostasis of vessel 560, e.g., when vessel 560 comprises a fully compressed vessel 520. In one or more embodiments, an application of a force to a lateral portion of forceps arms 100 may be configured to compress vessel 560 wherein vessel 560 maintains a symmetrical geometry with respect to a medial axis of vessel 560. Illustratively, vessel 560 may have a symmetrical geometry with respect to a medial axis of vessel 560 when vessel 560 comprises a fully compressed vessel 520. In one or more embodiments, forceps jaws 160 may be configured to compress vessel 560 wherein no portion of vessel 560 is compressed substantially more than another portion of vessel 560, e.g., forceps jaws 160 may be configured to evenly compress vessel 560 without pinching a first portion of vessel 560 or bulging a second portion of vessel 560. Illustratively, vessel 560 may be evenly compressed when vessel 560 comprises a fully compressed vessel 520.

In an embodiment of the bipolar forceps assembly 200, the forceps arm 100 is configured to efficiently transfer thermal energy or heat away from the conductor tips 110 at a rate sufficient to maintain the thermal energy of the conductor tips 100 below a designated threshold during operation of the bipolar forceps assembly 200. Below the designated threshold, the conductor tips 110 are less likely to damage targeted and non-targeted biological tissue, such as by sticking or charring, during operation. The designated threshold can vary according to a number of factors, such as, temperature, the type of biological tissue, the thermal conductivity or K-value (W/m K) of the material of the arms and conductor tips, operation time, and the like. For example, cellular response to temperature can generally be categorized as follows: 98.6° F. (37° C.) normal body temperature; about 122°–140° F. (50-60° C.) results in cell death over several minutes; about 194° F. (90° C.) causes instant cell death, protein denaturation, desiccation, and results in optimal "white" coagulation; about 212° F. (100° C.) vaporization, destructive expansion, vapor bubbles with arcing; and about 392° F. (200° C.) carbonization and charring. For another example, the thermal conductivity of copper is about 205% greater than aluminum, and 2300% greater than stainless steel (Half Hard Copper≈140 W/m K; Aluminum≈164 W/m K; Stainless Steel≈14.4 W/m K; Silver≈403 W/m K).

For efficient transfer of thermal energy, the forceps arm 100 can comprise a material having a thermal conductivity value greater than about 200 W/m K. For example, the material can comprise copper or copper alloy, including, but not limited to, pure copper (such as half hard or full hard heat treated copper), brass, copper-nickel, beryllium-copper, bronze, cupronickel, and the like. Although less cost-effective, the material properties of copper and/or copper alloy provide a higher thermal conductivity than other material typically used for bipolar forceps, such as, aluminum, stainless steel, and the like. In an exemplary embodiment, the forceps arm 100 is composed of a zirconium copper alloy having high thermal and electrical conductivity and characterized by high resistance to softening and resistance to deformation at high temperature, particularly when compared to pure copper.

In an embodiment of the bipolar forceps assembly 200, an outer surface 600 of the conductor tips 110 may be at least partially covered with a plating layer 602 having desirable material characteristics, such as, non-stick properties (FIG. 5A). For example, the plating layer 302 may be a plating material, such as silver or silver alloy due to their applicable material characteristics and cost. Generally, silver has applicable material characteristics for plating the conductor tips 110, including, high electrical conductivity, high thermal conductivity, biocompatibility, antimicrobial and antibacterial, and corrosion resistance. In addition, silver or silver alloy is cost-effective in comparison to other plating materials, such as, gold, platinum, and the like. The plating material can be any suitable silver alloy, including, but not limited to, pure silver, silver titanium, sterling silver, silver nickel, silver iron, and the like. However, alternate embodiments may use other suitable materials, such as, gold, platinum, and the like.

The plating layer 602 can be deposited onto the conductor tips 110 using any suitable process, including, but not limited to electroplating, electroless plating, electrolytic plating, and the like. In the illustrated embodiment, the plating layer 602 is deposited directly onto the outer surface 600 of the conductor tips 110. For example, the plating layer 602 of silver alloy is deposited directly onto at least a portion of the outer surfaces of the copper alloy conductor tips 110. In this way, using suitable materials, such as copper and silver, eliminates the need for additional intermediate plating layers, thereby reducing manufacturing cost.

In alternate embodiments, the application of the plating layer 602 may include additional steps. For example, the application of the plating layer 602 may include depositing multiple layers of the plating material. Alternatively, the application of the plating layer 602 may include depositing additional layers of other materials, such as, nickel, gold, platinum, palladium, rhodium, and the like. The application of the plating layer 602 may include surface preparation processes, such as, cleaning, removing ionic and non-ionic residues, applying organic solvent, applying water-soluble flux, During operation, thermal energy transfers from the conductor tips 110 through the forceps arms 100 and to the surrounding atmosphere. The combination of forceps arms 100 comprised of copper alloy and silver alloy plated conductor tips 110 provide a cost-effective bipolar forceps assembly 200 that can efficiently transfer thermal energy or heat away from the conductor tips 100 at a rate sufficient to maintain the thermal energy of the conductor tips 110 below the designated threshold during operation.

Figure 6:
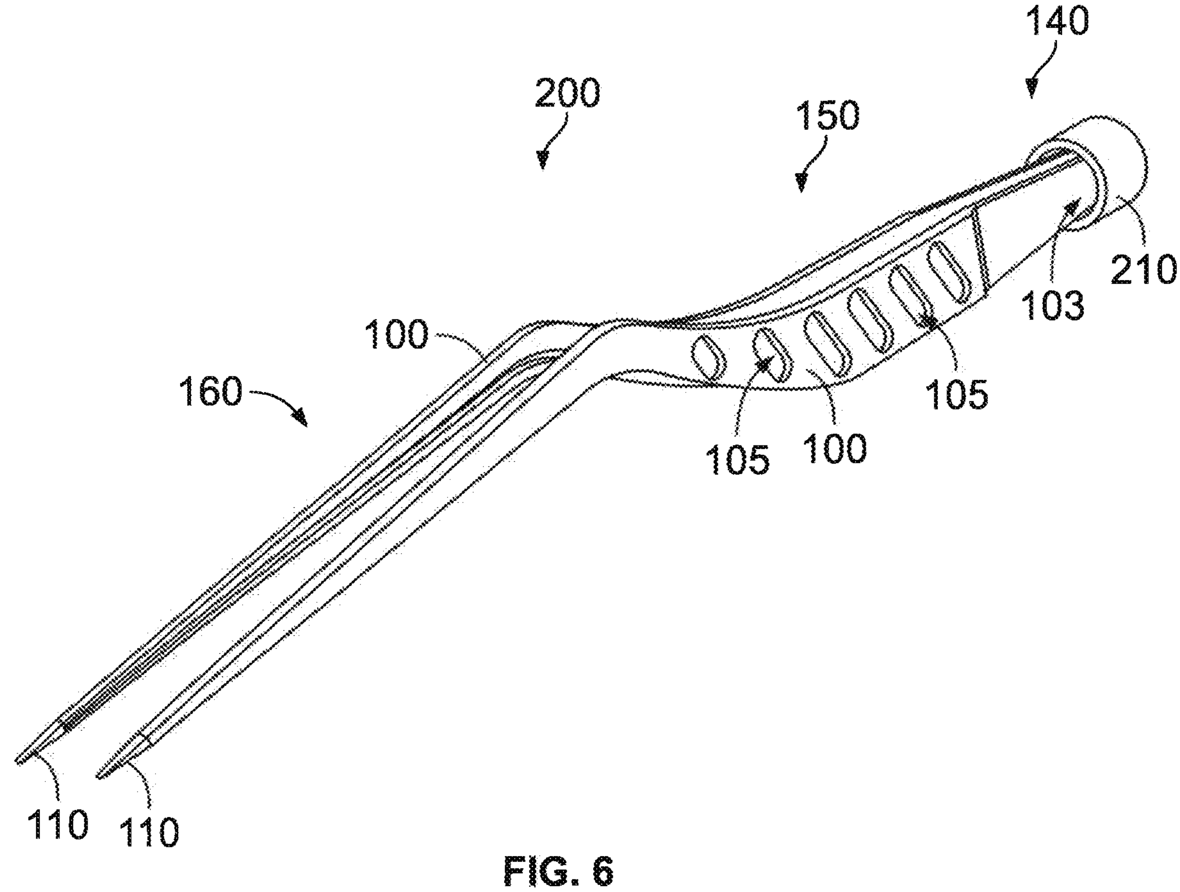
FIG. 6 is a schematic diagram of a bipolar forceps assembly 200 in accordance with an exemplary embodiment.

FIG. 6 is a schematic diagram of a bipolar forceps assembly 200 in accordance with an exemplary embodiment. In one or more embodiments, the bipolar forceps assembly 200 may comprise a pair of forceps arms 100 and an input conductor isolation mechanism 210, which may be connected to a bipolar cord (not shown). Illustratively, a portion of each forceps arm 100 may be coated with a material having a high electrical resistivity, e.g., a portion of each forceps arm 100 may be coated with an electrical insulator material. In one or more embodiments, conductor tips 110 of the forceps arms 100 may not be coated with a material.

In an exemplary embodiment, each forceps arm 100 includes the socket interface 140 connected to the input conductor isolation mechanism 210, the forceps arm grip 150 extending from the socket interface 140, and the forceps jaw 160 extending from the forceps arm grip 150. The forceps jaw 160 extends to the conductor tips 110. Illustratively, conductor tip 110 may be configured to prevent tissue from sticking to conductor tip 110. For example, the conductor tips 110 may have a plating layer at the working area. The material selected for the manufacture of the forceps arm 100 (for example, a zirconium copper alloy material) has efficient thermal conductivity to maintain or control temperature of the conductor tips 110 below a designated thermal threshold, such as corresponding to damaging of patient tissue. The socket interface 140 includes the input conductor housing 103 connected to the input conductor isolation mechanism 210.

The forceps arm grip 150 includes one or more forceps arm aperture(s) 105. In various embodiments, the forceps arm apertures 105 extend at least partially into the material of the forceps arm grip 150. Optionally, the forceps arm apertures 105 may extend entirely through the forceps arm grip 150. In other embodiments, the forceps arm apertures 105 extend partially through the forceps arm grip 150, such as into the inner side and/or the outer side of the forceps arm grip 150. Illustratively, forceps arm apertures 105 may be configured to reduce a mass of forceps arm 100. In one or more embodiments, forceps arm apertures 105 may be configured to decrease a thermal conductivity of forceps arm grip 150. In an exemplary embodiment, using closed bottom forceps arm apertures 105, as opposed to pass-through or completely open apertures, the forceps arm may have improved strength, which may allow thinning of the overall width of portions of the forceps arm 100, which may improve visibility of the working site and/or reduce weight of the bipolar forceps assembly 200.

The forceps arms 100 may be composed of any suitable material, e.g., polymers, metals, metal alloys, etc., or from any combination of suitable materials. In an exemplary embodiment, the forceps arms 100 may comprise an electrically conductive material. In one or more embodiments, forceps arms 100 may comprise an electrically conductive metal, e.g., silver, copper, gold, aluminum, etc. Forceps arms 100 may comprise an electrically conductive metal alloy. In an exemplary embodiment, forceps arms 100 comprise a copper alloy.

In an exemplary embodiment of the bipolar forceps 200, the forceps arm 100 is composed of a zirconium copper alloy. The zirconium copper forceps arm 100 comprises an alloy including both zirconium material and copper material. In various embodiments, the zirconium copper forceps arm 100 may consist only of zirconium and copper materials. In other various embodiments, the zirconium copper forceps arm 100 may consist essentially of zirconium and copper materials. In some embodiments, other metal materials may be included in the zirconium copper alloy material, such as chromium. The zirconium copper alloy may be Unified Numbering System (UNS) C15000 zirconium copper. The zirconium copper alloy may have between approximately 0.1% and Zirconium and between approximately 99.8% and 99.9% Copper in various embodiments. The zirconium copper alloy may have a higher or lower percentage of Zirconium in alternative embodiments. The zirconium copper alloy may be UNS C15100 zirconium copper having between approximately 0.05% and 0.15% Zirconium and between approximately 99.85% and 99.95% Copper in various embodiments. The zirconium copper alloy may be UNS C15150 zirconium copper having between approximately 0.15% and 0.30% Zirconium and between approximately 99.70% and 99.85% Copper in various embodiments. The zirconium copper alloy may be UNS C18150 copper chromium zirconium alloy having between approximately 0.02% and 0.25% Zirconium and between approximately 0.50% and 1.50% Chromium and the balance in Copper in various embodiments. The zirconium copper alloy may be UNS C17450-C17460 having approximately 0.50% Zirconium. The zirconium copper alloy may be used in the forceps arm grip 150 and/or the forceps jaw 160. However, in some embodiments, the forceps arm grip 150 may be manufactured from a different material from the forceps jaw 160, such as the forceps arm grip 150 manufactured from aluminum or an aluminum alloy and the forceps jaw 160 manufactured from the zirconium copper alloy.

In an exemplary embodiment, the zirconium copper alloy has higher softening temperature compared to copper. For example, the zirconium copper alloy may have greater than 10% increased softening temperature compared to copper. The zirconium copper alloy may have greater than 20% increased softening temperature compared to copper. The zirconium copper alloy may have greater than 50% increased softening temperature compared to copper. For example, the zirconium copper alloy may have a softening temperature resistance of 972 degrees Fahrenheit (500 degrees Celsius) where normally pure copper, by itself, can only stand up to 572 degrees Fahrenheit (300 degrees Celsius). The zirconium copper alloy has increased strength compared to copper. For example, the zirconium copper alloy may have greater than 10% increased strength compared to copper. The zirconium copper alloy may have greater than 20% increased strength compared to copper. For example, the zirconium copper alloy may have a tensile strength of 430 MPa where normally pure copper, by itself, has a tensile strength of 210 MPa. The zirconium copper alloy has improved thermal conductivity compared to conventional forceps materials, such as aluminum or stainless steel. For example, the zirconium copper alloy may have a thermal conductivity of 366.9 W/M K AT 20° C. (compared to Aluminum≈164 W/m K and Stainless Steel≈14.4 W/m K). The zirconium copper alloy has improved electrical conductivity compared to conventional forceps materials, such as aluminum or stainless steel. For example, the zirconium copper alloy may have an electrical conductivity of approximately 55×106 Siemens per meter at a temperature of 20.0° C. The zirconium copper alloy may have an electrical conductivity of approximately 93% IACS, whereas conventional forceps materials, such as aluminum has 61% IACS or stainless steel has 2.4% IACS. The zirconium copper alloy has a higher density and tensile strength compared to conventional forceps composed of aluminum materials. The increased strength of the zirconium copper alloy allows for thinning or reduction of material volume (and thus reduced weight and/or material cost) and/or the incorporation of pockets/apertures 105 to adjust for stiffness, flexibility, thermal conductivity, and electrical conductivity of the forceps while maintaining a performing state below the designated thermal threshold in a manner not possible with conventional aluminum forceps. The positive properties of the zirconium copper alloy allow for a reduction in material required to create forceps with better thermal performance compared to conventional iterations. The reduction in volume of material required to manufacture a copper zirconium embodiment of the forceps counteracts previously known issues with using copper as a forceps material associated with prohibitive cost. The strength of the zirconium copper alloy counteracts previous concerns with reliability of using copper forceps. Additionally, the zirconium copper alloy allows for a slimmer profile forceps jaw 160 with identical or better performance compared to traditional aluminum forceps designs allowing greater mobility, access and vision to surgeons as evidenced by decreased volume. The profile design of the zirconium copper alloy forceps arm is selected or designed based on the heavier weight and greater modulus of elasticity of the zirconium copper alloy material compared to the conventional aluminum forceps arm. The heavier weight of the zirconium copper alloy makes a thinner profile desirable to reduce the overall weight of the instrument. However, the greater modulus of elasticity makes a thinner profile less desirable because it reduces the stiffness of the instrument. Therefore, the overall profile balances these properties, in additional to considering other properties of the zirconium copper alloy material.

In an exemplary embodiment, the bipolar forceps assembly 200 composed of a zirconium copper alloy includes a structure that self-regulates a rate of thermal transfer to maintain the thermal energy below a designated thermal threshold. Therefore, the likelihood that biological tissue will stick or char is significantly reduced compared to a conventional bipolar forceps assembly composed of aluminum or stainless steel. The bipolar forceps assembly 200 composed of a zirconium copper alloy result in more efficient coagulation of biological tissue, which was more difficult to perform or control using conventional bipolar forceps assembly composed of aluminum or stainless steel. The results from the use of a zirconium copper alloy in the bipolar forceps assembly 200 is unexpected and counterintuitive due to the known material properties, including, heavy weight relative to existing materials (i.e steel and aluminum), low modulus of elasticity (i.e. very flexible) relative to existing materials, higher cost, and risk of copper toxicity to patients.

FIG. 7 is a table comparing properties of an aluminum alloy (UNS 6061 or UNS 6061-T6 or UNS A96061) typical of conventional forceps arm and a zirconium copper alloy (UNS C15000) for embodiments of the forceps arm 100 described herein. The table shows that the zirconium copper alloy has greater tensile strength compared to the aluminum alloy. The table shows that the zirconium copper alloy has greater modulus of elasticity compared to the aluminum alloy. The table shows that the zirconium copper alloy has greater shear modulus and shear strength compared to the aluminum alloy. The table shows that the zirconium copper alloy has improved electrical conductivity compared to the aluminum alloy. The table shows that the zirconium copper alloy has improved thermal conductivity compared to the aluminum alloy. The zirconium copper alloy allows a reduced volume with greater performance below the designated thermal threshold compared to the conventional aluminum forceps iterations.

FIG. 8 is a table showing thermal potential of the zirconium copper alloy in various embodiments of the forceps arm 100 compared to aluminum embodiments having equivalent forceps lengths. In all sizes (for example, 7", 8", 9"), the zirconium copper alloy functions better (for example, approximately 30-50% higher thermal potential) than the aluminum alloy counterparts, allowing better thermal management and control of the operating temperature of the conductor tips 110.

FIG. 9 is a table showing electrical conductivity of the zirconium copper alloy in various embodiments of the forceps arm 100 compared to aluminum embodiments having equivalent forceps lengths. In all sizes (for example, 7", 8", 9"), the zirconium copper alloy functions better (for example, approximately 30-50% higher electrical conductivity) than the aluminum alloy counterparts. The zirconium copper alloy possesses greater electrical conductivity rates than identical aluminum alloy embodiments, allowing use of smaller forceps arms and/or lower power for better temperature control of the conductor tips 110.

FIG. 10 is a table showing a volumetric comparison between zirconium copper alloy and aluminum alloy forceps embodiments. The zirconium copper alloy embodiments have greater thermal potential and electrical conductivity, allowing for a reduction in volume compared to their aluminum alloy counterparts while maintaining performance below the designated thermal threshold. The volumetric reduction allowed by the zirconium copper alloy increases visibility. The material of the zirconium copper alloy embodiments allows improved thermal control of the conductor tips by reducing the thermal mass of the material at the ends of the forceps arm 100 to keep the conductor tips 100 below a designated threshold temperature, which may correspond to damaging of patient tissue, making the conductor tips 110 less likely to damage targeted and non-targeted biological tissue, such as by sticking or charring, during operation.

Figures 11A, 11B:
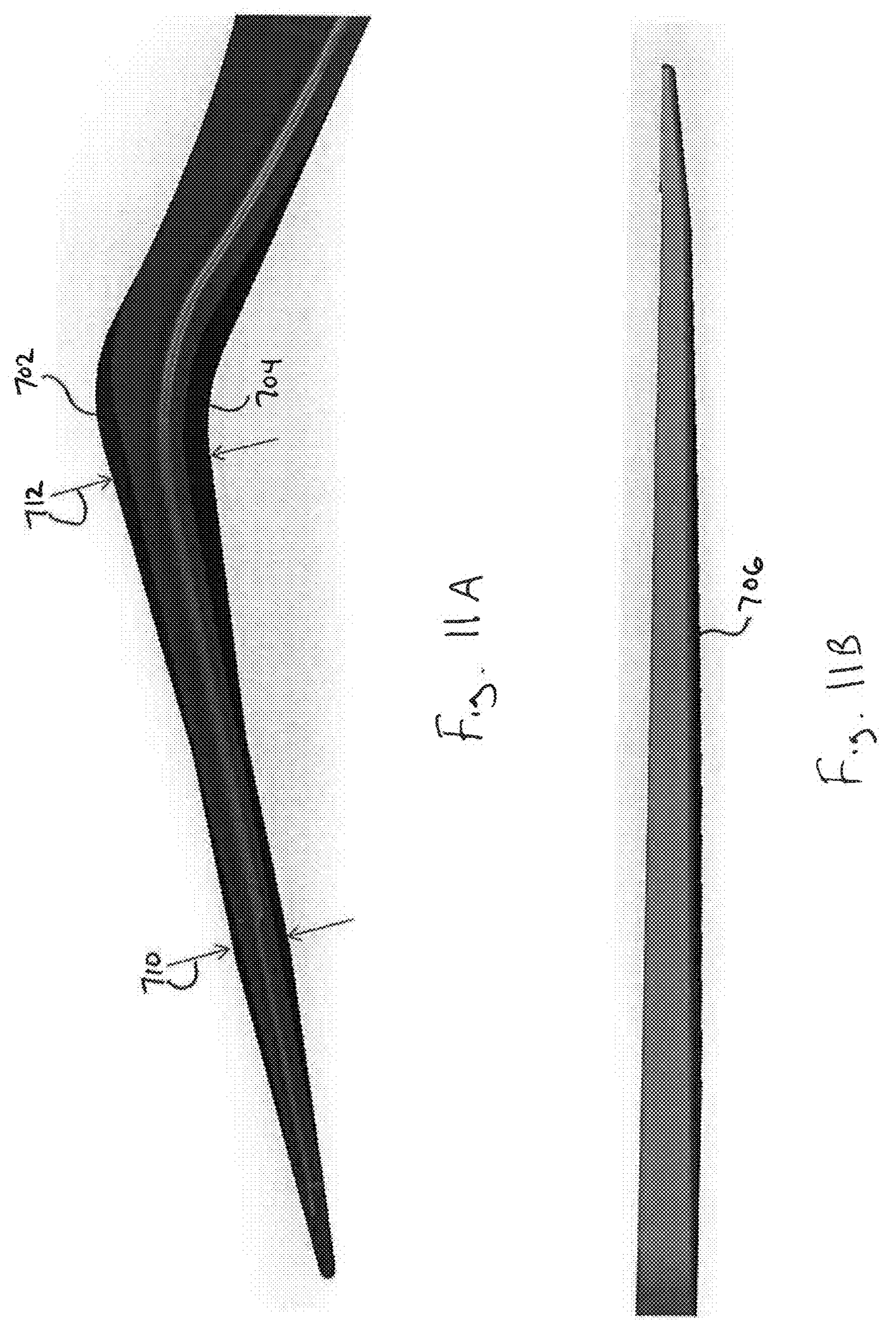
FIG. 11A is a side view of the forceps arm 100 in accordance with an exemplary embodiment showing a 7" zirconium copper alloy embodiment.
FIG. 11B is a top view of the forceps arm 100 in accordance with an exemplary embodiment showing a 7" zirconium copper alloy embodiment.

FIG. 11A is a side view of the forceps arm 100 in accordance with an exemplary embodiment showing a 7" zirconium copper alloy embodiment. FIG. 11B is a top view of the forceps arm 100 in accordance with an exemplary embodiment showing a 7" zirconium copper alloy embodiment. FIGS. 11A and 11B illustrate removed areas 702, 704, 706 compared to an equivalent aluminum alloy counterpart forceps arm. The width at section 710 may be 0.1019" for the zirconium copper alloy embodiment and 0.1519" for the equivalent aluminum alloy embodiment. The width at section 712 may be 0.1555" for the zirconium copper alloy embodiment and 0.2722" for the equivalent aluminum alloy embodiment. The zirconium copper alloy embodiment is shorter and narrower than the equivalent aluminum alloy embodiment, which reduces weight of the forceps arm 100, while maintaining equivalent or better rigidity than the aluminum counterpart while removing mass from the working length in order to give a slimmer profile. The slimmer profile allows for better visibility and access to locations during surgery.

Figures 12A, 12B, 12C:
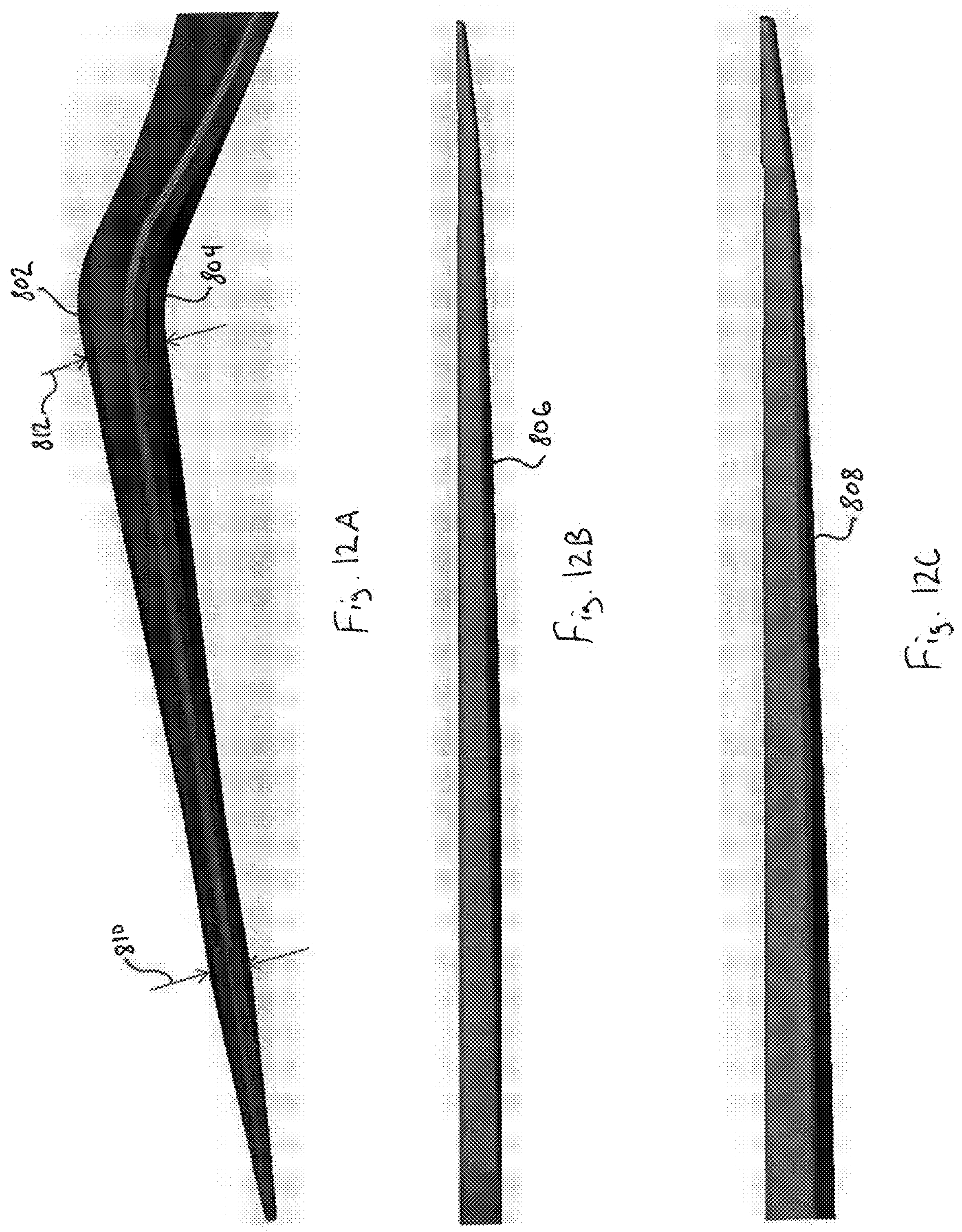
FIG. 12A is a side view of the forceps arm 100 in accordance with an exemplary embodiment showing a 8" zirconium copper alloy embodiment.
FIG. 12B is a top view of the forceps arm 100 in accordance with an exemplary embodiment showing a 8" zirconium copper alloy embodiment.
FIG. 12C is a bottom view of the forceps arm 100 in accordance with an exemplary embodiment showing a 8" zirconium copper alloy embodiment.

FIG. 12A is a side view of the forceps arm 100 in accordance with an exemplary embodiment showing a 8" zirconium copper alloy embodiment. FIG. 12B is a top view of the forceps arm 100 in accordance with an exemplary embodiment showing a 8" zirconium copper alloy embodiment. FIG. 12C is a bottom view of the forceps arm 100 in accordance with an exemplary embodiment showing a 8" zirconium copper alloy embodiment. FIGS. 12A, 12B, 12C illustrate removed areas 802, 804, 806, 808 compared to an equivalent aluminum alloy counterpart forceps arm. The width at section 810 may be 0.1019" for the zirconium copper alloy embodiment and 0.1519" for the equivalent aluminum alloy embodiment. The width at section 812 may be 0.1955" for the zirconium copper alloy embodiment and 0.3066" for the equivalent aluminum alloy embodiment. The zirconium copper alloy embodiment is shorter and narrower than the equivalent aluminum alloy embodiment, which reduces weight of the forceps arm 100, while maintaining equivalent or better rigidity than the aluminum counterpart while removing mass from the working length in order to give a slimmer profile. The slimmer profile allows for better visibility and access to locations during surgery. In various embodiments, for the 8", 1.0 mm (for example, middle sized forceps) handle the zirconium copper alloy embodiment has a total volume for one handle of 2652.01 mm^3 corresponding to an the equivalent aluminum version having a volume of 4065.27 mm^3. As such, the removed areas 802, 804, 806, 808 may correspond to a volume reduction of 1413.26 mm^3. For the working length (for example, jaw portion 160) the zirconium copper alloy embodiment has a volume of 703.08 mm^3 while the aluminum equivalent embodiment has a volume of 1157.67 mm^3. As such, the removed areas 802, 804, 806, 808 may correspond to a volume reduction of 454.59 mm^3 in the jaw portion 160.

Figures 13A, 13B, 13C:
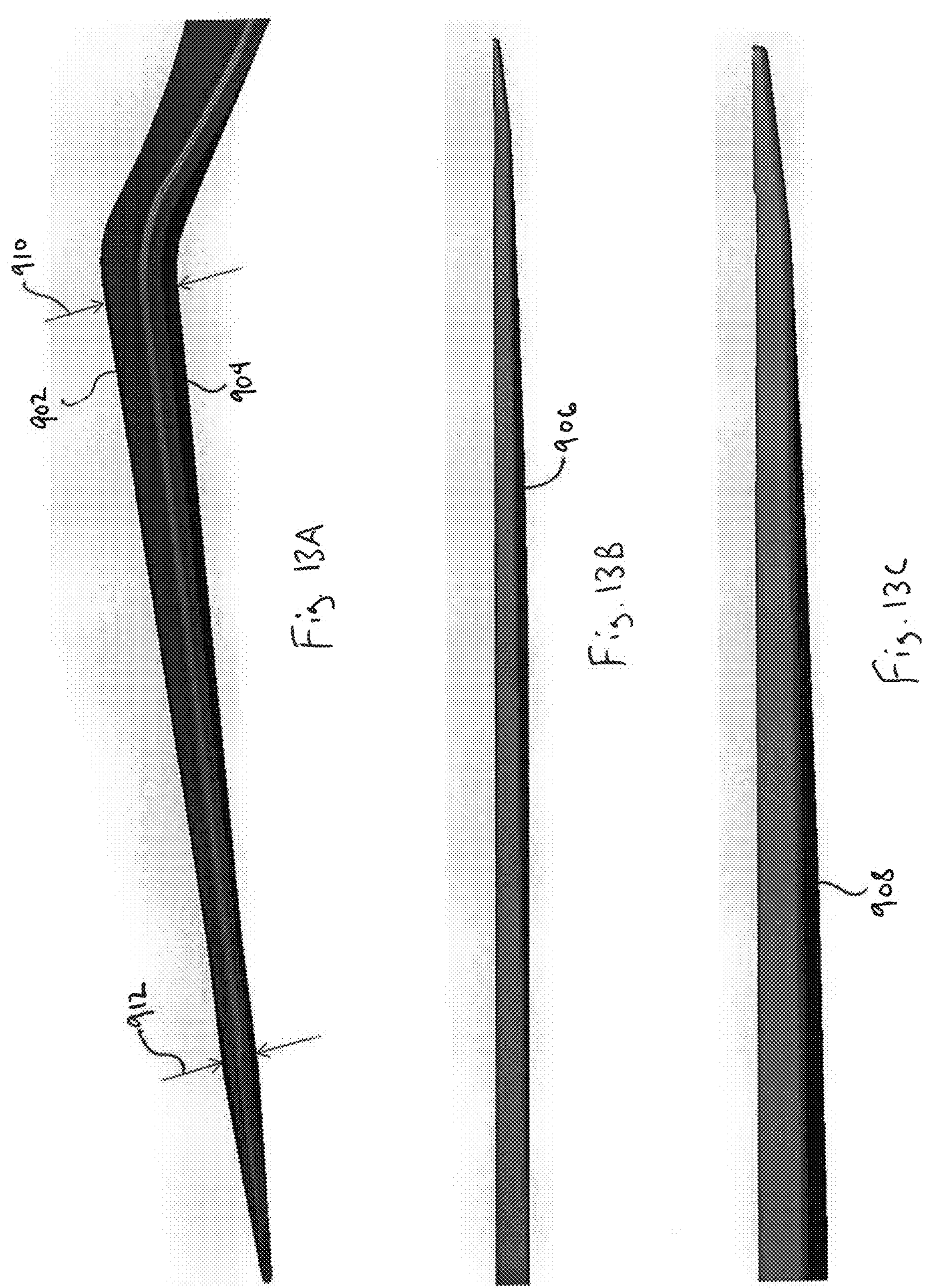
FIG. 13A is a side view of the forceps arm 100 in accordance with an exemplary embodiment showing a 9" zirconium copper alloy embodiment.
FIG. 13B is a top view of the forceps arm 100 in accordance with an exemplary embodiment showing a 9" zirconium copper alloy embodiment.
FIG. 13C is a bottom view of the forceps arm 100 in accordance with an exemplary embodiment showing a 9" zirconium copper alloy embodiment.

FIG. 13A is a side view of the forceps arm 100 in accordance with an exemplary embodiment showing a 9" zirconium copper alloy embodiment. FIG. 13B is a top view of the forceps arm 100 in accordance with an exemplary embodiment showing a 9" zirconium copper alloy embodiment. FIG. 13C is a bottom view of the forceps arm 100 in accordance with an exemplary embodiment showing a 9" zirconium copper alloy embodiment. FIGS. 13A, 13B, 13C illustrate removed areas 902, 904, 906, 908 compared to an equivalent aluminum alloy counterpart forceps arm. The width at section 910 may be 0.1019" for the zirconium copper alloy embodiment and 0.1519" for the equivalent aluminum alloy embodiment. The width at section 912 may be 0.2400" for the zirconium copper alloy embodiment and 0.3228" for the equivalent aluminum alloy embodiment. The zirconium copper alloy embodiment is shorter and narrower than the equivalent aluminum alloy embodiment, which reduces weight of the forceps arm 100, while maintaining equivalent or better rigidity than the aluminum counterpart while removing mass from the working length in order to give a slimmer profile. The slimmer profile allows for better visibility and access to locations during surgery.

In some example embodiments, a surgical instrument for electrosurgery includes a first forceps arm having a first forceps arm distal end and a first forceps arm proximal end, a first forceps jaw of the first forceps arm having a first forceps jaw distal end and a first forceps jaw proximal end wherein the first forceps jaw distal end is the first forceps arm distal end, a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, a second forceps arm having a second forceps arm distal end and a second forceps arm proximal end, the second forceps arm disposed opposite the first forceps arm, a second forceps jaw of the second forceps arm having a second forceps jaw distal end and a second forceps jaw proximal end, the second forceps jaw disposed opposite the first forceps jaw wherein the second forceps jaw distal end is the second forceps arm distal end, a second conductor tip of the second forceps arm having a second conductor tip distal end and a second conductor tip proximal end, and the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end. The first forceps arm and the second forceps arm are configured to transfer thermal energy away from the first conductor tip and second conductor tip at a rate sufficient to maintain the temperature of the first conductor tip and second conductor tip s below a designated temperature. The first and second forceps arms being composed of a zirconium copper alloy.

Optionally, the first forceps arm and the second forceps arm may include a zirconium copper alloy having between 0.105% and 0.250% zirconium. The first forceps arm and the second forceps arm may include a zirconium copper alloy having between 0.10% and 0.20% zirconium. The first forceps arm and the second forceps arm may include a zirconium copper alloy having between 97.0% and 99.9% copper. The first forceps arm and the second forceps arm may include a zirconium copper alloy having a chemical composition of UNS 15000. The first forceps arm and the second forceps arm may include a material having a thermal conductivity higher than about 360 W/m K. The first forceps arm and the second forceps arm may include a material having a tensile strength higher than about 400 MPa.

In an aspect, a plating layer may cover at least a portion of the first conductor tip of the first forceps arm. The plating layer may include a silver alloy. The plating layer may be deposited directly to an outer surface of at least the portion of the first conductor tip.

In an aspect, a coating of an electrical insulator material may be applied over at least a portion of the first forceps arm and at least a portion of the second forceps arm.

Optionally, the first forceps arm may include a first forceps arm aperture, wherein the first forceps arm aperture is configured to reduce a mass of the first forceps arm and the second forceps arm may include a second forceps arm aperture, wherein the second forceps arm aperture is configured to reduce a mass of the second forceps arm. The first forceps arm aperture may extend entirely through the first forceps arm and the second forceps arm aperture may extend entirely through the second forceps arm. The first forceps arm aperture may extend only partially through the first forceps arm and the second forceps arm aperture may extend only partially through the second forceps arm. The first forceps arm aperture may be one of a plurality of first forceps arm apertures in the first forceps arm. The second forceps arm aperture may be one of a plurality of second forceps arm apertures in the second forceps arm.

Optionally, the surgical instrument is configured to be disposable.

In another embodiment, a surgical instrument for electrosurgery includes a first forceps arm having a first forceps arm distal end and a first forceps arm proximal end, a first forceps jaw of the first forceps arm having a first forceps jaw distal end and a first forceps jaw proximal end wherein the first forceps jaw distal end is the first forceps arm distal end, a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, the first conductor tip having a first plating layer deposited directly to at least a portion of an outer surface of the first conductor tip, a second forceps arm having a second forceps arm distal end and a second forceps arm proximal end, the second forceps arm disposed opposite the first forceps arm, a second forceps jaw of the second forceps arm having a second forceps jaw distal end and a second forceps jaw proximal end, the second forceps jaw disposed opposite the first forceps jaw wherein the second forceps jaw distal end is the second forceps arm distal end, a second conductor tip of the second forceps arm having a second conductor tip distal end and a second conductor tip proximal end, and the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end, the second conductor tip having a second plating layer deposited directly to at least a portion of an outer surface of the second conductor tip. The first forceps arm and the second forceps arm are configured to transfer thermal energy away from the first conductor tip and second conductor tip at a rate sufficient to maintain the temperature of the first conductor tip and second conductor tip s below a designated temperature. The first and second forceps arms being composed of a zirconium copper alloy.

In another embodiment, a method of manufacturing a surgical instrument includes providing a first forceps arm having a first forceps arm distal end and a first forceps arm proximal end, providing a first forceps jaw of the first forceps arm having a first forceps jaw distal end and a first forceps jaw proximal end wherein the first forceps jaw distal end is the first forceps arm distal end, providing a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, providing a second forceps arm having a second forceps arm distal end and a second forceps arm proximal end, the second forceps arm disposed opposite the first forceps arm, providing a second forceps jaw of the second forceps arm having a second forceps jaw distal end and a second forceps jaw proximal end, the second forceps jaw disposed opposite the first forceps jaw wherein the second forceps jaw distal end is the second forceps arm distal end, providing a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end, depositing a first plating layer directly onto at least a portion of an a first outer surface of the first conductor tip, and depositing a second plating layer directly onto at least a portion of a second outer surface of the second conductor tip. The first forceps arm and the second forceps arm are configured to transfer thermal energy away from the first conductor tip and second conductor tip at a rate sufficient to maintain the temperature of the first conductor tip and second conductor tip s below a designated temperature. The first and second forceps arms being composed of a zirconium copper alloy.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, communication unit, control system, etc.) may be implemented in a single piece of hardware (for example, a general-purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

Changes can be made in the above constructions without departing from the scope of the disclosure, it is intended that all matter contained in the above description or shown in the accompanying drawings shall be interpreted as illustrative and not in a limiting sense.

What is claimed is:

1. A surgical instrument for electrosurgery, comprising:

a first forceps arm having a first forceps arm distal end and a first forceps arm proximal end, the first forceps arm composed of a zirconium copper alloy;

a first forceps jaw of the first forceps arm having a first forceps jaw distal end and a first forceps jaw proximal end wherein the first forceps jaw distal end is the first forceps arm distal end;

a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end;

a second forceps arm having a second forceps arm distal end and a second forceps arm proximal end, the second forceps arm disposed opposite the first forceps arm, the second forceps arm composed of a zirconium copper alloy;

a second forceps jaw of the second forceps arm having a second forceps jaw distal end and a second forceps jaw proximal end, the second forceps jaw disposed opposite the first forceps jaw wherein the second forceps jaw distal end is the second forceps arm distal end;

a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end; and wherein the first forceps arm and the second forceps arm are configured to transfer thermal energy away from the first conductor tip and second conductor tip at a rate sufficient to maintain the thermal energy of the first conductor tip and second conductor tip below a designated thermal threshold.

2. The surgical instrument of claim 1, wherein the first forceps arm and the second forceps arm comprise the zirconium copper alloy having between 0.05% and 0.50% zirconium.

3. The surgical instrument of claim 1, wherein the first forceps arm and the second forceps arm comprise the zirconium copper alloy having between 0.10% and 0.20% zirconium.

4. The surgical instrument of claim 1, wherein the first forceps arm and the second forceps arm comprise the zirconium copper alloy having between 97.0% and 99.9% copper.

5. The surgical instrument of claim 1, wherein the first forceps arm and the second forceps arm comprise the zirconium copper alloy having a chemical composition of UNS 15000.

6. The surgical instrument of claim 1, wherein the zirconium copper alloy of the first forceps arm and the second forceps arm has a thermal conductivity higher than about 360 W/m K.

7. The surgical instrument of claim 1, wherein the zirconium copper alloy of the first forceps arm and the second forceps arm has a tensile strength higher than about 400 MPa.

8. The surgical instrument of claim 7, wherein the plating layer comprises a silver alloy.

9. The surgical instrument of claim 7, the plating layer being deposited directly to an outer surface of at least the portion of the first conductor tip.

10. The surgical instrument of claim 1, further comprising a plating layer covering at least a portion of the first conductor tip of the first forceps arm.

11. The surgical instrument of claim 1, further comprising a coating of an electrical insulator material over at least a portion of the first forceps arm and at least a portion of the second forceps arm.

12. The surgical instrument of claim 11, wherein the first forceps arm aperture extends entirely through the first forceps arm, and wherein the second forceps arm aperture extends entirely through the second forceps arm.

13. The surgical instrument of claim 11, wherein the first forceps arm aperture extends only partially through the first forceps arm, and wherein the second forceps arm aperture extends only partially through the second forceps arm.

14. The surgical instrument of claim 11, wherein the first forceps arm aperture is one of a plurality of first forceps arm apertures in the first forceps arm, and wherein the second forceps arm aperture is one of a plurality of second forceps arm apertures in the second forceps arm.

15. The surgical instrument of claim 1, further comprising:

- a first forceps arm aperture of the first forceps arm, wherein the first forceps arm aperture is configured to reduce a mass of the first forceps arm; and
- a second forceps arm aperture of the second forceps arm, wherein the second forceps arm aperture is configured to reduce a mass of the second forceps arm.

16. A surgical instrument for electrosurgery, comprising:

- a first forceps arm having a first forceps arm distal end and a first forceps arm proximal end, the first forceps arm composed of a zirconium copper alloy;
- a first forceps jaw of the first forceps arm having a first forceps jaw distal end and a first forceps jaw proximal end wherein the first forceps jaw distal end is the first forceps arm distal end;
- a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end, the first conductor tip having a first plating layer deposited directly to at least a portion of an outer surface of the first conductor tip;
- a second forceps arm having a second forceps arm distal end and a second forceps arm proximal end, the second forceps arm disposed opposite the first forceps arm, the second forceps arm composed of a zirconium copper alloy;
- a second forceps jaw of the second forceps arm having a second forceps jaw distal end and a second forceps jaw proximal end, the second forceps jaw disposed opposite the first forceps jaw wherein the second forceps jaw distal end is the second forceps arm distal end;
- a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end, the second conductor tip having a second plating layer deposited directly to at least a portion of an outer surface of the second conductor tip; and
- wherein the first forceps arm and the second forceps arm are configured to transfer thermal energy away from the first conductor tip and second conductor tip at a rate sufficient to maintain the thermal energy of the first conductor tip and second conductor tip below a designated thermal threshold.

17. The surgical instrument of claim 16, wherein the first forceps arm and the second forceps arm comprise the zirconium copper alloy having between 0.05% and 0.50% zirconium.

18. The surgical instrument of claim 17, wherein the zirconium copper alloy of the first forceps arm and the second forceps arm has a thermal conductivity higher than about 360 W/m K.

19. The surgical instrument of claim 16, wherein the first forceps arm and the second forceps arm comprise the zirconium copper alloy having between 0.10% and 0.20% zirconium.

20. The surgical instrument of claim 16, wherein the first forceps arm and the second forceps arm comprise the zirconium copper alloy having between 97.0% and 99.9% copper.

21. The surgical instrument of claim 16, wherein the zirconium copper alloy of the first forceps arm and the second forceps arm has a tensile strength higher than about 400 MPa.

22. The surgical instrument of claim 16, further comprising:

- a first forceps arm aperture of the first forceps arm, wherein the first forceps arm aperture is configured to reduce a mass of the first forceps arm; and
- a second forceps arm aperture of the second forceps arm, wherein the second forceps arm aperture is configured to reduce a mass of the second forceps arm.

23. The surgical instrument of claim 16, wherein the first plating layer and the second plating layer comprise a silver alloy.

24. A method of manufacturing a surgical instrument, comprising:

providing a first forceps arm having a first forceps arm distal end and a first forceps arm proximal end, the first forceps arm composed of a zirconium copper alloy;

providing a first forceps jaw of the first forceps arm having a first forceps jaw distal end and a first forceps jaw proximal end wherein the first forceps jaw distal end is the first forceps arm distal end;

providing a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end;

providing a second forceps arm having a second forceps arm distal end and a second forceps arm proximal end, the second forceps arm disposed opposite the first forceps arm, the second forceps arm composed of a zirconium copper alloy;

providing a second forceps jaw of the second forceps arm having a second forceps jaw distal end and a second forceps jaw proximal end, the second forceps jaw disposed opposite the first forceps jaw wherein the second forceps jaw distal end is the second forceps arm distal end;

providing a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end; and depositing a first plating layer directly onto at least a portion of a first outer surface of the first conductor tip;

depositing a second plating layer directly onto at least a portion of a second outer surface of the second conductor tip;

wherein the first forceps arm and the second forceps arm are configured to transfer thermal energy away from the first conductor tip and second conductor tip at a rate sufficient to maintain the thermal energy of the first conductor tip and second conductor tip below a designated thermal threshold.

* * * * *